(12) United States Patent
Ruch Werneck Guimarães et al.

(10) Patent No.: US 10,781,182 B2
(45) Date of Patent: Sep. 22, 2020

(54) COMPOUNDS, PROCESS FOR OBTAINING THE COMPOUNDS, PHARMACEUTICAL COMPOSITION, USE OF THE COMPOUNDS AND METHOD FOR TREATING PSYCHIATRIC DISORDERS AND/OR SLEEP DISORDERS

(71) Applicant: ACHÉ LABORATÓRIOS FARMACÊUTICOS S.A., Guarulhos (BR)

(72) Inventors: Cristiano Ruch Werneck Guimarães, São Paulo (BR); Hatylas Felype Zaneti De Azevedo, São Paulo (BR); Alessandra Mascarello, Guarulhos (BR); Renata Watanabe Da Costa, São Paulo (BR); Valter Freire Torres Russo, Itapira (BR); Elisa Mannochio De Souza Russo, Itapira (BR)

(73) Assignee: ACHÉ LABORATÓRIOS FARMACÊUTICOS S.A., Guarulhos (BR)

( * ) Notice: Subject to any disclaimer, the term of this patent is extended or adjusted under 35 U.S.C. 154(b) by 0 days.

(21) Appl. No.: 16/344,721

(22) PCT Filed: Oct. 23, 2017

(86) PCT No.: PCT/BR2017/050320
§ 371 (c)(1),
(2) Date: Apr. 24, 2019

(87) PCT Pub. No.: WO2018/076090
PCT Pub. Date: May 3, 2018

(65) Prior Publication Data
US 2019/0270711 A1    Sep. 5, 2019

(30) Foreign Application Priority Data

Oct. 24, 2016 (BR) .......................... 102016024814

(51) Int. Cl.
| | | |
|---|---|---|
| C07D 235/26 | (2006.01) |
| C07D 235/28 | (2006.01) |
| C07D 491/048 | (2006.01) |
| A61P 25/24 | (2006.01) |
| A61P 25/20 | (2006.01) |
| A61P 25/22 | (2006.01) |

(52) U.S. Cl.
CPC ............ *C07D 235/26* (2013.01); *A61P 25/20* (2018.01); *A61P 25/22* (2018.01); *A61P 25/24* (2018.01); *C07D 235/28* (2013.01); *C07D 491/048* (2013.01)

(58) Field of Classification Search
CPC .................................................. C07D 235/26
See application file for complete search history.

(56) References Cited

U.S. PATENT DOCUMENTS

| | | |
|---|---|---|
| 6,376,666 B1 | 4/2002 | Seredenin et al. |
| 2007/0191447 A1 | 8/2007 | Kodo et al. |
| 2009/0298811 A1 | 12/2009 | Ando et al. |
| 2010/0056515 A1 | 3/2010 | Aso et al. |
| 2011/0245231 A1 | 10/2011 | Ivashchenko et al. |

OTHER PUBLICATIONS

International Search Report dated Jul. 12, 2017 in International Application No. PCT/BR2017/050320.
Seredenin, SB, Voronin MV. Neuroreceptor mechanisms involved in the action of afobazole. Eksperimental'naya Klinicheskaya Farmakologiya, vol. 72(1): pp. 3-11, 2009.
Voronin, MK, Kadnikov, IA. Contribution of sigma-1 receptor to cytoprotective effect of afobazole. Pharmacology Research & Perspectives, vol. 4(6): pp. 1-8, 2016.

*Primary Examiner* — Golam M Shameem
(74) *Attorney, Agent, or Firm* — B. Aaron Schulman, Esq.; Stites & Harbison, PLLC

(57) ABSTRACT

The present invention relates to novel and inventive pharmacologically active benzimidazole derivative compounds, which surprisingly have high affinity for melatonin $MT_1$ and $MT_2$ receptors and low affinity for CYP450 complex enzymes, specially CYP1A2. The present invention also relates to novel and inventive routes of synthesis of these compounds, pharmaceutical compositions comprising the compounds and the use of these compounds in the treatment of individuals affected by psychiatric disorders and/or sleep disorders related to these receptors (specially depression, anxiety, circadian cycle disorders), in addition to process for producing the composition.

6 Claims, 3 Drawing Sheets

A                                B

Figure 1:
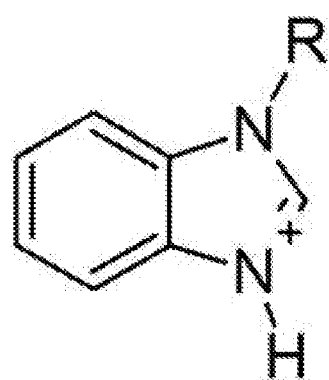
Figure 1:
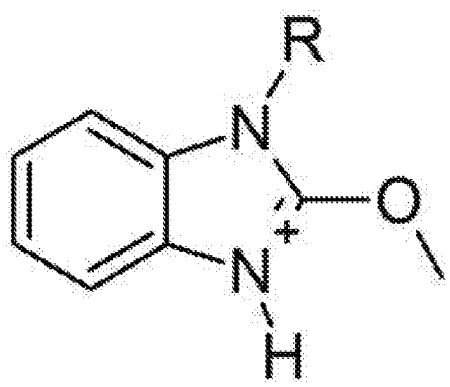

Epik => p$K_a$ = 6.10 ± 2.22    Epik => p$K_a$ = 5.65 ± 2.22
Jaguar => p$K_a$ = 6.0          Jaguar => p$K_a$ = 5

COMPOUNDS, PROCESS FOR OBTAINING THE COMPOUNDS, PHARMACEUTICAL COMPOSITION, USE OF THE COMPOUNDS AND METHOD FOR TREATING PSYCHIATRIC DISORDERS AND/OR SLEEP DISORDERS

FIELD OF THE INVENTION

The present invention relates to novel and inventive pharmacologically active benzimidazole derivative compounds, which have affinity for melatonergic receptors, specially MT1 and MT2, showing high bioavailability and decreased drug-drug interaction potential. Novel and inventive routes of synthesis are also described for these compounds, as well as pharmaceutical compositions comprising these compounds and their use in the treatment of individuals affected by psychiatric disorders and/or sleep disorders related to such receptors, such as depression, anxiety, insomnia and circadian cycle disorders. The present invention is in the field of pharmacy, medicine and chemistry.

BACKGROUND OF THE INVENTION

According to the World Health Organization (WHO) estimates, over 350 million people worldwide suffer from depression. According to this estimate, depression is common in every region of the world and it is related to social, psychological and biological factors, and may be associated with other disorders such as anxiety and sleep disorders. The earlier a treatment for these disorders is started, the more efficient it is. From the biological stand point, several treatments are now being used and each of them has advantages and disadvantages, as described below.

One of the treatments for psychiatric disorders and sleep disorders is the simulation of the physiological effects of melatonin. Melatonin is a natural hormone widely present in a variety of organisms, such as bacteria, unicellular algae, fungi, plants, vertebrates and mammals, including humans. In mammals, melatonin is mainly produced by the pineal gland and released into the blood stream following the circadian rhythm, reaching a high plasma concentration at night (Zlotos, D. P., Jockers, R., Cecon, E., Rivara, S., & Witt-Enderby, P. A. (2014). *MT1 and MT2 melatonin receptors: ligands, models, oligomers, and therapeutic potential. Journal of Medicinal Chemistry*, 57(8), 3161-3185.).

The physiological effects of melatonin are mediated by the activation of G protein-coupled melatonergic receptors, which have been named $MT_1$ and $MT_2$. Both receptors are present in mammals, including humans. Melatonin has a variety of activities, including chronobiotic, hypnotic, antioxidative, oncostatic, immunoregulatory activities and it is also linked to the reproductive cycle management, controlling the onset of puberty. Its contribution in the regulation of human mood and behavior has arisen significant clinical attention. Deficiencies in melatonin production or in the expression of its receptors, as well as changes in rhythm and range of melatonin secretion, have shown importance in breast cancer, neurodegenerative diseases and in Parkinson's and Alzheimer's diseases, in addition to some neurological disorders in children, conditions such as chronic insomnia and sleep disorders related to the circadian cycle. However, although widely available, commercial melatonin has an unfavorable pharmacokinetic profile due to its high first pass metabolism, very short half-life and high pharmacokinetic inter-individual variability.

Recently, the implication of melatonin in neuropsychiatric disorders, such as major depressive disorder, has arisen special attention due to the development of the molecule agomelatine, a melatonergic agonist that targets MT1 and MT2 receptors. (V. Srinivasan, Amnon Brzezinski, SukruOter and Samuel D. Shillcutt, in *Melatonin and Melatonergic Drugs in Clinical Practice*—2014th Ed.—pg. v).

Agomelatine and ramelteon are two examples of commercially available melatonergic compounds; although considered effective, present non optimal pharmacokinetics for oral drugs, as explained below. Agomelatine, described in the document EP 0 447 285 by Andrieux et al. describes compounds of general formula:

which are useful in the treatment of central nervous system diseases. Similarly, U.S. Pat. No. 6,034,239 by Ohkawa et al. describes ramelteon as part of the compounds of general formula:

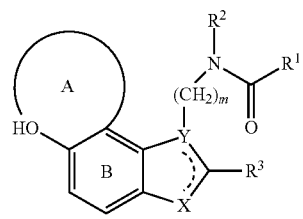

wherein R1 is an optionally substituted hydrocarbon group, an optionally substituted amino group or an optionally substituted heterocyclic group; R2 represents a hydrogen or an optionally substituted hydrocarbon group; R3 represents a hydrogen atom, an optionally substituted hydrocarbon group or an optionally substituted heterocyclic group; X represents CHR4, NR4, O or S, wherein R4 represents a hydrogen atom or an optionally substituted hydrocarbon group; Y is C, CH or N, provided that when X is CH2, Y is C or CH; the dashed line represents a single or double bond; A represents an optionally substituted 5- to 7-membered oxygen-containing heterocyclic ring; ring B represents an optionally substituted benzene ring and m represents a full figure from 1 to 4.

Agomelatine and ramelteon have appropriate oral absorption. However, both compounds undergo extensive hepatic (or first pass) metabolism, resulting in low absolute bioavailabilities, which are estimated to be 1% for agomelatine and 1.8% for ramelteon (respectively: Valdoxan—Product Information—Australia, and Pandi-Perumal et al., Pharmacotherapy of insomnia with ramelteon: safety, efficacy and clinical applications, Journal of Central Nervous System Disease 2011, 3, 51-65). The low bioavailability due to extensive metabolism leads to highly variable pharmacokinetic profiles for both drugs among individuals. The main metabolite of ramelteon, which is characterized by hydroxylation of the secondary carbon in the R1 group, is also active and, therefore, the action of the drug depends on its metabolism, which compromises drug efficacy due to the population heterogeneity.

Bioavailability is one of the most important properties in oral drugs. A high oral bioavailability allows a reduction in dose, enough to achieve proper pharmacological effect, reducing the risk of side effects and toxicity. A low bioavailability may result in low efficacy and high inter-individual variability, which may trigger unpredictable responses to the drug.

Therefore, if we only consider the unmet need for new drugs for psychiatric disorders and/or sleep disorders along with the bioavailability problems already described for the commercially available melatonergic agonists, it is possible to observe the need for development of new drugs that overcome these disadvantages. In addition, some melatonergic agonists, such as agomelatine, show additional disadvantages specially in relation to drug interaction and hepatotoxicity, as explained below.

Agomelatine tends to interact with proteins naturally involved with the metabolism of xenobiotic compounds, such as liver cytochrome enzymes (CYP450). Around 90% of agomelatine is metabolized in the liver by the P450 cytochrome 1A2 (CYP1A2) enzyme and 10% by cytochromes CYP2C9 and CYP2C19, with a high first pass metabolism, as previously mentioned. One possible metabolite of agomelatine is 3,4-epoxide, which is highly reactive and can covalently modify important proteins, probably being responsible for liver toxicity.

As it is a CYP1A2 substrate, the concomitant administration of agomelatine with other drugs that interact with this isoform (such as fluvoxamine and ciprofloxacin) is not recommended, as described in the package leaflet for the reference drug for agomelatine, Valdoxan. Since these drugs are potent inhibitors of CYP1A2, their concomitant administration with agomelatine inhibits its metabolism and may lead to elevated plasma concentrations.

According to a recent statement issued by the European Medicine Agency (EMA), other drugs that are moderate inhibitors of CYP1A2, such as propranolol, and CYP1A2 inducers, such as rifampicin, also should not be administered concomitantly with agomelatine since they alter its metabolism, which may lead to liver toxicity (specially in the case of inducers). In addition, the fact that agomelatine metabolism is dependent on CYP2C9 and CYP2C19, two highly polymorphic proteins in the population, makes the metabolism of this drug highly variable in patients, which leads to an additional risk.

Thus, there is an evident need for the development of new drugs that overcome agomelatine bioavailability issues, and are also capable of reducing potential adverse effects related to liver metabolism. Therefore, there is a great interest in the development of synthetic molecules targeting the melatonergic system and that are more suitable for patients. Particularly, drugs from this class that do not interact with CYP enzymes, specially CYP1A2, would provide therapeutic and safety advantages for patients. (Mor, M. et al. Recent advances in the development of melatonin MT(1) and MT(2) receptor agonists. Expert Opinion on Therapeutic Patents 2010, 20(8), 1059-1077).

In the state of the art, several melatonin receptor ligands from different structural classes are described and will be mentioned here only as reference of the state of the art, since none of them show the advantages of the present invention.

Several of these ligands have been designed comprising the bicyclic indole ring substitution present in melatonin with other bicyclic or non-bicyclic bioisosteric rings, such as naphthalene, benzofuran, benzothiophene, benzoxazole, indane, tetralin, quinoline, phenyl, among many others, without considerable detriment to the high affinity to receptors. The wide variety of the bioisosteric indole nuclei described in the state of the art seems to indicate that the nature of the aromatic ring type of different ligands is less relevant for the affinity with melatonin receptors.

An exception to this rule is observed when the bicyclic nucleus of the ligand, e.g. melatonin indolic nucleus, is substituted by a benzimidazole nucleus. In this case, a decrease in the affinity for the melatonergic receptors is observed in comparison to ligands comprising other nuclei (Zlotos, D P, Jockers, R., Cecon, E., Rivara, S., & Witt-Enderby, P A,—MT1 and MT2 melatonin receptors: ligands, models, oligomers, and therapeutic potential Journal of Medicinal Chemistry, 57 (8), 3161-3185 Zlotos, D P (2005) Recent advances in melatonin receptor ligands Archiv Der Pharmazie (Weinheim), 338(5-6), 229-247; Cathy D. Mahle, Katherine S. Takaki and A. John Watson in Annual Reports in Medicinal Chemistry vol. 32, pg. 36 e Melatonin and Melatonergic Drugs in Clinical Practice—V. Srinivasan, Amnon Brzezinski, SukruOter and Samuel D. Shillcutt, 2014th Ed.—pg. 99).

Although many compounds with high affinity for melatonin receptors have been described to date, references of compounds which have affinity and which show a benzimidazole type bicyclic ring as central nucleus are remarkably rare. The main references related to derivatives containing a benzimidazole nucleus are described below.

In U.S. Pat. No. 5,276,051, along with its divisions U.S. Pat. Nos. 5,308,866 and 5,380,750, Lesieur et al. describe melatonin agonist compounds comprising various types of bicyclic rings, among them, indole, benzothiophene, benzimidazole, benzoisoxazole, benzoisothiazole and indazole. In this document, the compound shown in example 57 is N-[2-(6-methoxybenzimidazol-1-yl)-ethyl]acetamide, corresponding to the melatonin analogue in which the indole nucleus is substituted by benzimidazole. Although this document does not disclose detailed information regarding affinity for the described compounds, the affinity of the compound in example 57 was published in a later study, where different melatonin analogs were analyzed for their affinities. Under assay conditions, the affinity of this benzimidazole derivative was found to be approximately 3,200 times lower than melatonin affinity (Depreux, P., Lesieur, D., Mansour, H. A., Morgan, P., Howell, H. E., Renard, P., et al. (1994) Synthesis and Structure-Activity Relationships of Novel Naphthalene and Bioisosteric Related Amidic Derivatives as Melatonin Receptor Ligands Journal of Medicinal Chemistry, 37 (20), 3231-3239; P. A. Witt-Enderby, P-K. Li, Vitamin and Hormones, 2000, 58, 321-354).

Depreux et al (Synthetic Communications 1994, 24 (15), 2123-2132) describe melatonin-like benzimidazole compounds that were also described in U.S. Pat. No. 5,260,051. Among synthesized compounds, it is the abovementioned benzimidazole analogue of melatonin. In this document, no data regarding the affinities of these compounds to melatonin receptors are reported.

In U.S. Pat. No. 5,496,826 are described compounds of formula:

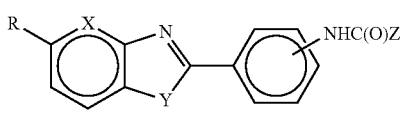

wherein R=H or C1-4 alkoxy; X=CH or N; y=NH, O or S; Z=C1-4 alkyl, C3-6 cycloalkyl, C2-3 alkenyl, NH2, C1-4 alkylamino, or C1-4 alkoxyalkyl, except that Z cannot be CH3 when R=H, X=CH and y=NH and Z cannot be CH3 when R=H, X=N and y=NH and NHC(O)Z is in the "para" position. Among the disclosed compounds are benzimidazoles with anticonvulsive properties.

Other examples of melatonergic compounds that do not contain benzimidazole nuclei and therefore are not relevant to the present invention, are mentioned as state of the art and can be found in: EP 0 506 539, WO 1997/11056, WO99/62515, WO95/17405, U.S. Pat. Nos. 5,856,529, 6,211,225.

However, all compounds described in the state of the art usually do not have good affinity to melatonergic receptors, making them less suitable for therapeutic use.

Thus, the present invention addresses this gap with novel compounds comprising benzimidazole nucleus with novel and inventive substituents. In these compounds, the carbon between the nitrogen of the benzimidazole ring is bonded to an oxygen or sulfur atom, followed by an alkyl chain. These compounds have high affinity for the melatonergic receptors MT1 and MT2 and have low affinity for the CYP450 complex enzymes. Thus, these compounds show a promising pharmacokinetic profile, with high bioavailability; additionally, it is possible to avoid liver problems, including those resulting from drug interactions. The compounds of the present invention are useful in the treatment of subjects affected with psychiatric disorders and/or sleep disorders mediated by or associated with these receptors, such as disorders related to sleep and circadian cycle, jet lag, chronic insomnia and/or psychiatric disorders such as major depressive disorder, seasonal depression, and anxiety.

Based on a literature survey, no documents were found anticipating or suggesting the findings of the present invention, so that the technical solution here proposed has novelty and inventive activity compared to the state of the art.

SUMMARY OF THE INVENTION

In one aspect, the present invention relates to novel and inventive pharmacologically active benzimidazole derivative compounds with high bioavailability and reduced drug-drug interaction effects. More specifically, they have high affinity for melatonin MT1 and MT2 receptors and have no affinity for CYP enzymes, specially CYP1A2. The method for obtaining the route of synthesis for these compounds, pharmaceutical compositions and their use in the treatment of individuals affected with psychiatric disorders and/or sleep disorders are also described.

Therefore, it is the first object of the present invention to provide the compound of general formula (I):

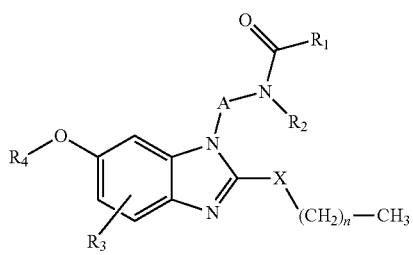

wherein
X represents an oxygen or sulfur atom;
A represents a linear alkyl group of C2-4 which may have one or more hydrogens substituted by an alkyl group selected from methyl, ethyl, propyl or isopropyl;
R1 is a C1-6 alkyl group, or C2-6 alkenyl, or C2-6 alkynyl, or C1-6 haloalkyl, or C3-6 cycloalkyl, or C1-2 alkyl-C3-6 cycloalkyl;
R2 represents a hydrogen or a C1-3 alkyl group;
R3 represents a hydrogen or a halogen atom;
R4 is a C1-6 alkyl group;
n is 0 or 1.

It is also an object of the present invention the compound of general formula (II):

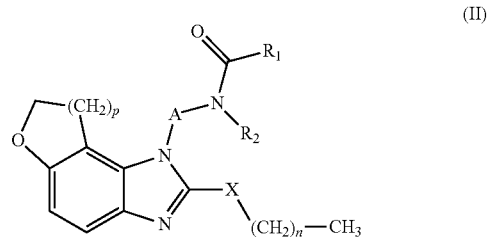

wherein
X represents an oxygen or sulfur atom;
A represents a linear alkyl group of C2-4 which may have one or more hydrogens substituted by an alkyl group selected from methyl, ethyl, propyl or isopropyl;
R1 is a C1-6 alkyl group, or C2-6 alkenyl, or C2-6 alkynyl, or C1-6 haloalkyl, or C3-6 cycloalkyl, or C1-2 alkyl-C3-6 cycloalkyl;
R2 represents a hydrogen or a C1-3 alkyl group;
n is 0 or 1;
p is 1 or 2.

A further object of the present invention is a process of obtaining the compound of general formula (I), comprising the following steps:
(a) reacting of a compound of formula (III)

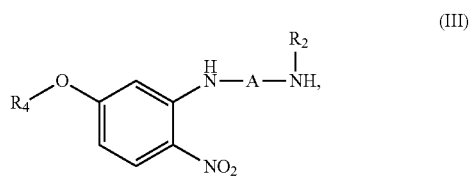

with a carboxylic acid anhydride of formula (IV)

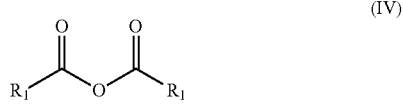

or with a carboxylic acid halide of formula (V)

Wherein R1, R2 and R4 are as described for the compound of general formula (I) and X1 is a halogen selected from the group comprising chlorine and bromine, to obtain a compound of formula (VI)

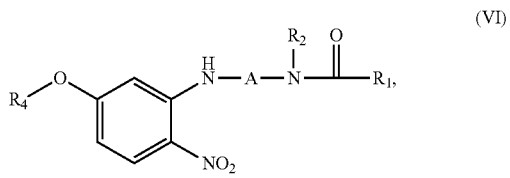

(b) reacting the compound (VI) obtained in step (a) with a reducing agent to obtain the compound of formula (VII)

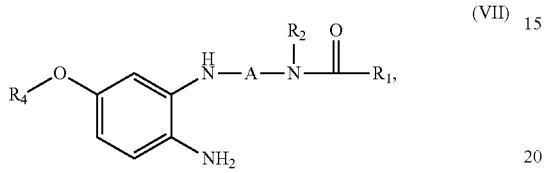

(c) reacting the compound (VII) obtained in step (b) with a tetraalkylorthocarbonate selected from the group comprising the tetramethylorthocarbonate and tetraethyl orthocarbonate, to obtain the compound of formula (Ia)

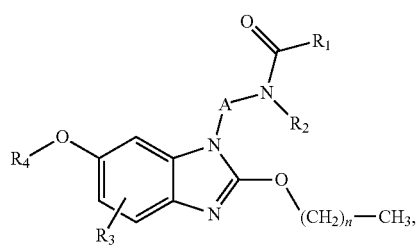

wherein R3 represents a hydrogen atom and "n" represents zero or one.

In addition to the aforementioned step, the process for obtaining the compound of general formula (I) can further comprise the step of:

(d) reacting the compound of formula (Ia) obtained in step (c) with a halogenating agent selected from the group comprising N-bromosuccinimide, N-chlorosuccinimide and N-iodosuccinimide, to obtain the compound of formula (Ia), wherein R3 represents a halogen selected from the group comprising bromine, chlorine and iodine.

In another embodiment, the process of obtaining the compound of general formula (I) of the present invention comprises the steps of:

(a) reacting the compound of formula (III)

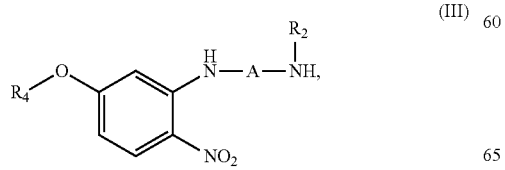

with a carboxylic acid anhydride of formula (IV)

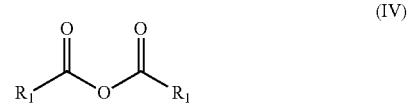

or with a carboxylic acid halide of formula (V)

wherein R1, R2 and R4 are as described for the compound of formula (I) and X1 represents a halogen selected from the group comprising chlorine and bromine, to obtain a compound of formula (VI)

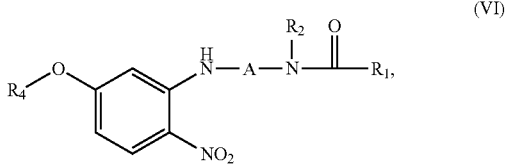

(b) reacting the compound (VI) obtained in step (a) with a reducing agent to obtain the compound of formula (VII)

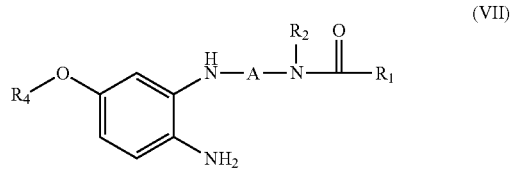

(e) reacting the compound (VII) obtained in step (b) with thiourea in order to obtain the compound (VIII)

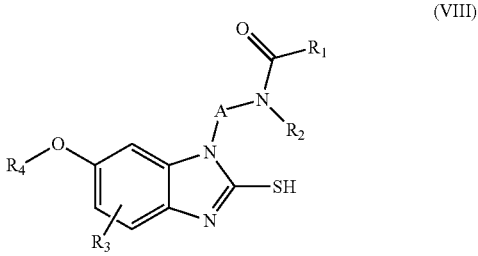

wherein R3 represents a hydrogen atom;

(f) reacting the compound (VIII) obtained in step (e) with an alkylating agent to obtain the compound of formula (Ib)

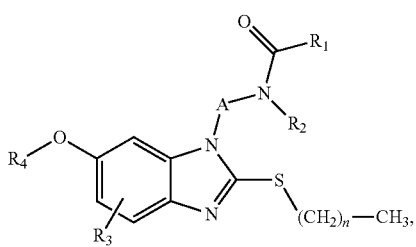
(Ib)

wherein R3 represents a hydrogen atom and "n" represents zero or one;

(g) reacting the compound of formula (Ib) obtained in step (f) with a halogenating agent selected from the group comprising N-bromosuccinimide, N-chlorosuccinimide and N-iodosuccinimide, to obtain the compound of general formula (Ib) wherein R3 represents a halogen selected from the group comprising bromine, chlorine and iodine.

Another object of the present invention is the process for obtaining the compound of general formula (II) comprising the following steps:

(a) reacting the compound of formula (IX)

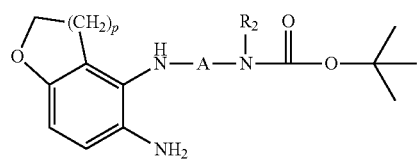
(IX)

with a tetraalkylorthocarbonate selected from the group comprising tetramethylorthocarbonate and tetraethyl orthocarbonate, to give a compound of formula (X)

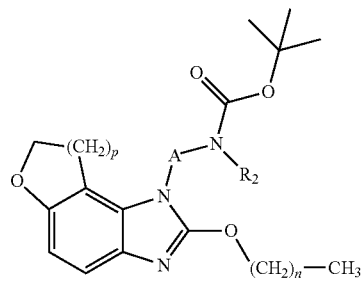
(X)

wherein R2, "n" and "p" are as described for the compound of formula (I) or (II);

(b) reacting the compound of formula (X) obtained in step (a) with a deprotecting agent to obtain a compound of formula (XI)

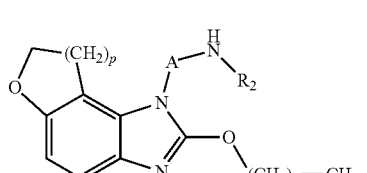
(XI)

(c) reacting of the compound of formula (XI) obtained in (b) with a carboxylic acid anhydride of formula (IV)

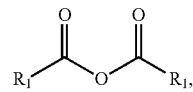
(IV)

or with a carboxylic acid halide of formula (V)

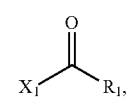
(V)

to obtain the compound of formula (IIa),

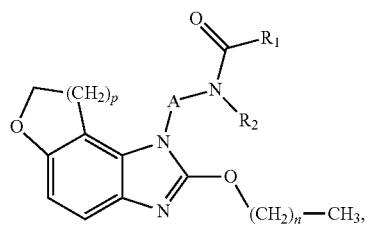
(IIa)

wherein R1 is as described for the compound of formula (II) and X1 represents a bromine or chlorine atom;

(d) reacting the compound of formula (IX)

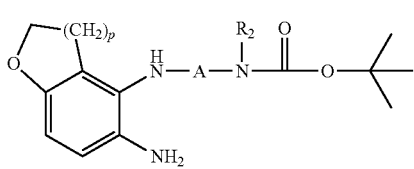
(IX)

with thiourea, obtaining the compound of formula (XII)

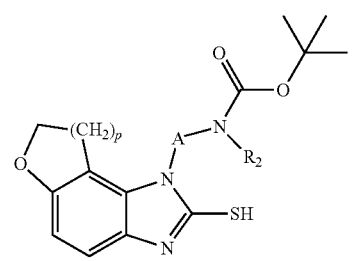
(XII)

(e) reacting the compound of formula (XII) obtained in step (d) with an alkylating agent to obtain the compound of formula (XIII)

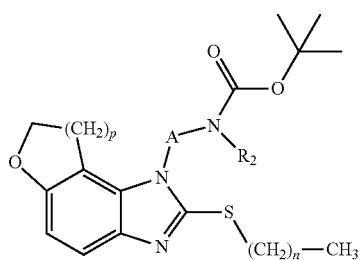

(XIII)

wherein "n" is as described for the compound of formulae (I) or (II);

(f) reacting the compound obtained in (e) with a deprotecting agent to obtain a compound of formula XIV:

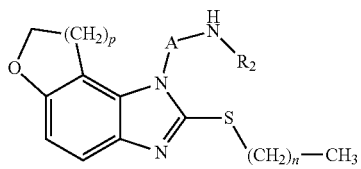

(XIV)

(g) reacting the compound of formula (XIV) obtained in (f) with a carboxylic acid anhydride of formula (IV)

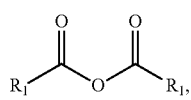

(IV)

or with a carboxylic acid halide of formula (V)

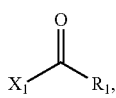

(V)

to obtain the compound of formula (IIb):

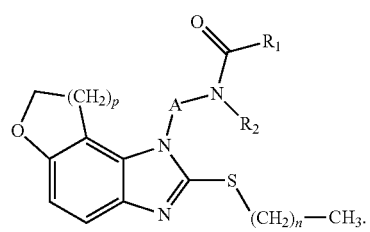

(IIb)

A further object of the present invention is a pharmaceutical composition characterized for comprising a compound of general formula (I):

a)

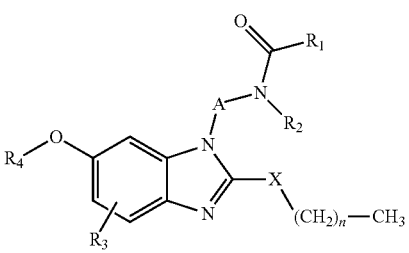

(I)

wherein

X represents an oxygen or sulfur atom;

A represents a linear alkyl group of C2-4 which may have one or more hydrogens substituted by an alkyl group selected from methyl, ethyl, propyl or isopropyl;

R1 represents a C1-6 alkyl group, or C2-6 alkenyl, or C2-6 alkynyl, or C1-6 haloalkyl, or C3-6 cycloalkyl, or C1-2 alkyl-C3-6 cycloalkyl;

R2 represents a hydrogen or a C1-3 alkyl group;

R3 represents a hydrogen or a halogen atom;

R4 represents a C1-6 alkyl group;

n is 0 or 1; and b) at least one pharmaceutically acceptable vehicle.

A further object of the present invention is a pharmaceutical composition characterized for comprising a compound of general formula (II):

(a)

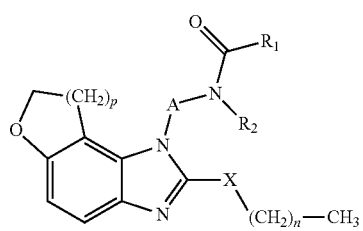

(II)

wherein

X represents an oxygen or sulfur atom;

A represents a linear C2-4 alkyl group which may have one or more hydrogens substituted by an alkyl group selected from methyl, ethyl, propyl or isopropyl;

R1 is a C1-6 alkyl group, or C2-6 alkenyl, or C2-6 alkynyl, or C1-6 haloalkyl, or C3-6 cycloalkyl, or C1-2 alkyl-C3-6 cycloalkyl;

R2 represents a hydrogen or a C1-3 alkyl group;

n is 0 or 1;

p is 1 or 2; and b) at least one pharmaceutically acceptable vehicle.

In addition, a further object of the present invention is the use of the compound of general formula (I):

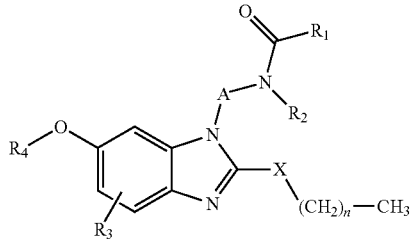

(I)

wherein

X represents an oxygen or sulfur atom;

A represents a linear alkyl group of C2-4 which may have one or more hydrogens substituted by an alkyl group selected from methyl, ethyl, propyl or isopropyl;

R1 represents a C1-6 alkyl group, or C2-6 alkenyl, or C2-6 alkynyl, or C1-6 haloalkyl, or C3-6 cycloalkyl, or C1-2 alkyl-C3-6 cycloalkyl;

R2 represents a hydrogen or a C1-3 alkyl group;

R3 represents a hydrogen or halogen atom;

R4 represents a C1-6 alkyl group, n is 0 or 1;

in the manufacture of a drug for the treatment of psychiatric disorders and/or sleep disorders.

In addition, a further object of the present invention is the use of the compound of general formula (II):

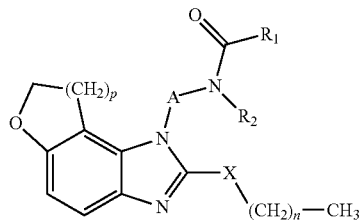

(II)

wherein

X represents an oxygen or sulfur atom;

A represents a linear alkyl group of C 2-4 which may have one or more hydrogens substituted by an alkyl group selected from methyl, ethyl, propyl or isopropyl;

R1 represents a C1-6 alkyl group, or C2-6 alkenyl, or C2-6 alkynyl, or C1-6 haloalkyl, or C3-6 cycloalkyl, or C1-2 alkyl-C3-6 cycloalkyl;

R2 represents a hydrogen or a C1-3 alkyl group;

n is 0 or 1;

p is 1 or 2, in the manufacture of a drug for the treatment of psychiatric disorders and/or sleep disorders.

Another object of the present invention is a method of treating psychiatric disorders and/or sleep disorders, which comprises in administering to a mammal a therapeutically effective amount of the compound of general formula(I):

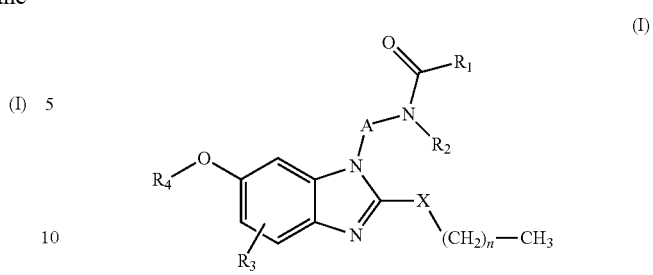

(I)

wherein

X represents an oxygen or sulfur atom;

A represents a linear alkyl group of C2-4 which may have one or more hydrogens substituted by an alkyl group selected from methyl, ethyl, propyl or isopropyl;

R1 represents a C1-6 alkyl group, or C2-6 alkenyl, or C2-6 alkynyl, or C1-6 haloalkyl, or C3-6 cycloalkyl, or C1-2 alkyl-C3-6 cycloalkyl;

R2 represents a hydrogen or a C1-3 alkyl group;

R3 represents a hydrogen or a halogen atom;

R4 represents a C1-6 alkyl group, n is 0 or 1.

Another object of the present invention is a method of treating psychiatric disorders and/or sleep disorders, which comprises administering to a mammal a therapeutically effective amount of the compound of general formula (II):

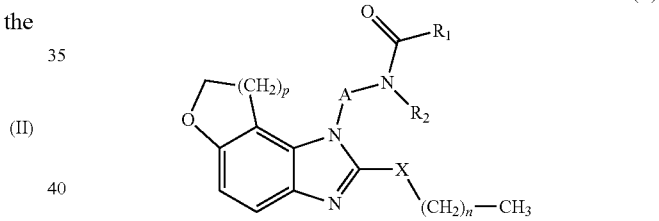

(II)

wherein

X represents an oxygen or sulfur atom;

A represents a linear alkyl group of C 2-4 which may have one or more hydrogens substituted by an alkyl group selected from methyl, ethyl, propyl or isopropyl;

R1 represents a C1-6 alkyl group, or C2-6 alkenyl, or C2-6 alkynyl, or C1-6 haloalkyl, or C3-6 cycloalkyl, or C1-2 alkyl-C3-6 cycloalkyl;

R2 represents a hydrogen or a C1-3 alkyl group;

n is 0 or 1;

p is 1 or 2.

DETAILED DESCRIPTION OF FIGURES

FIG. 1. Calculation of pKa values for benzimidazole (A) and its derivative substituted with a methoxy group at the 2-position of ring (B).

Figure 2:
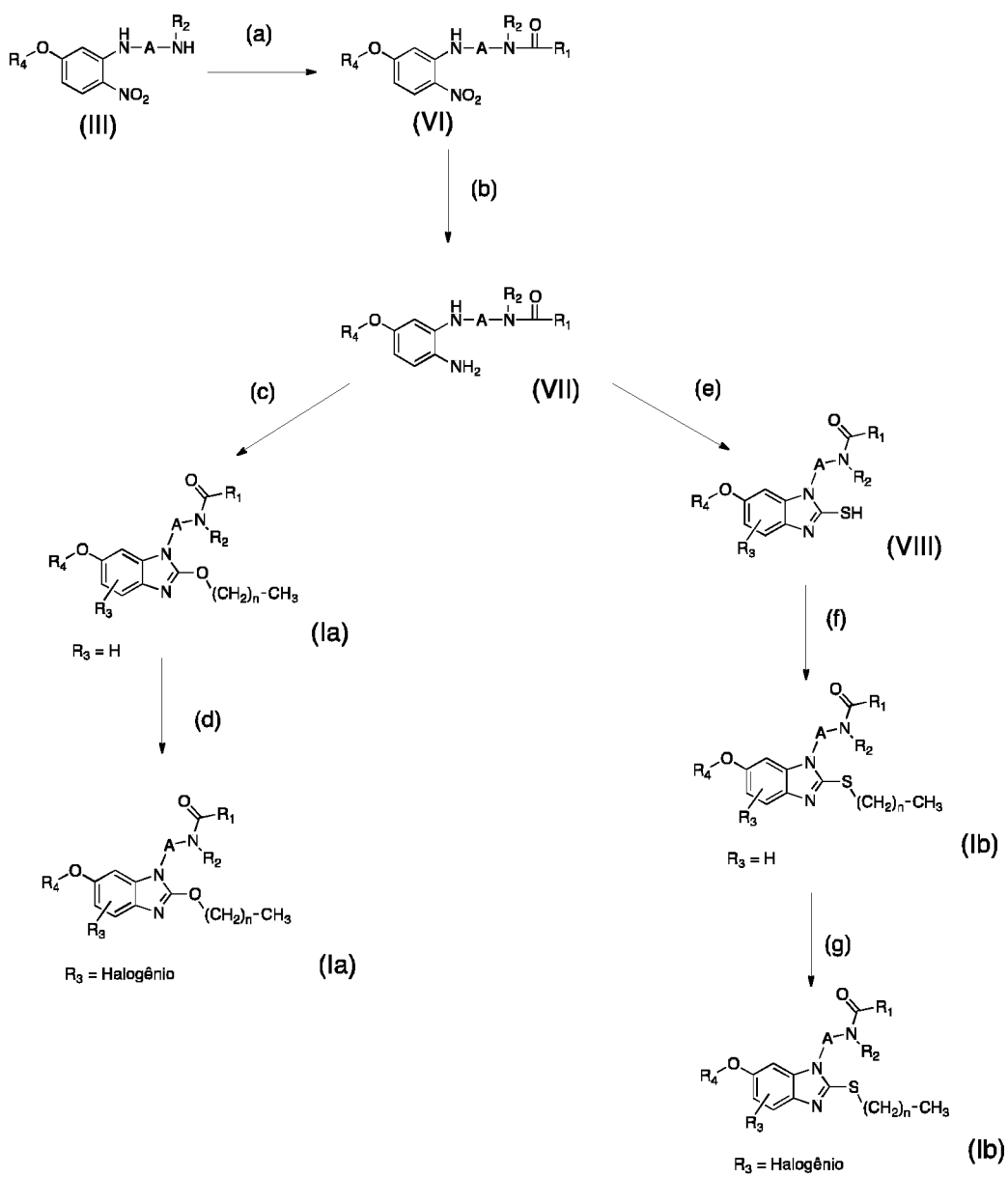

FIG. 2. Example of the process for obtaining the compound of general formula (I), including compounds of formulae (Ia) and (Ib).

Figure 3:
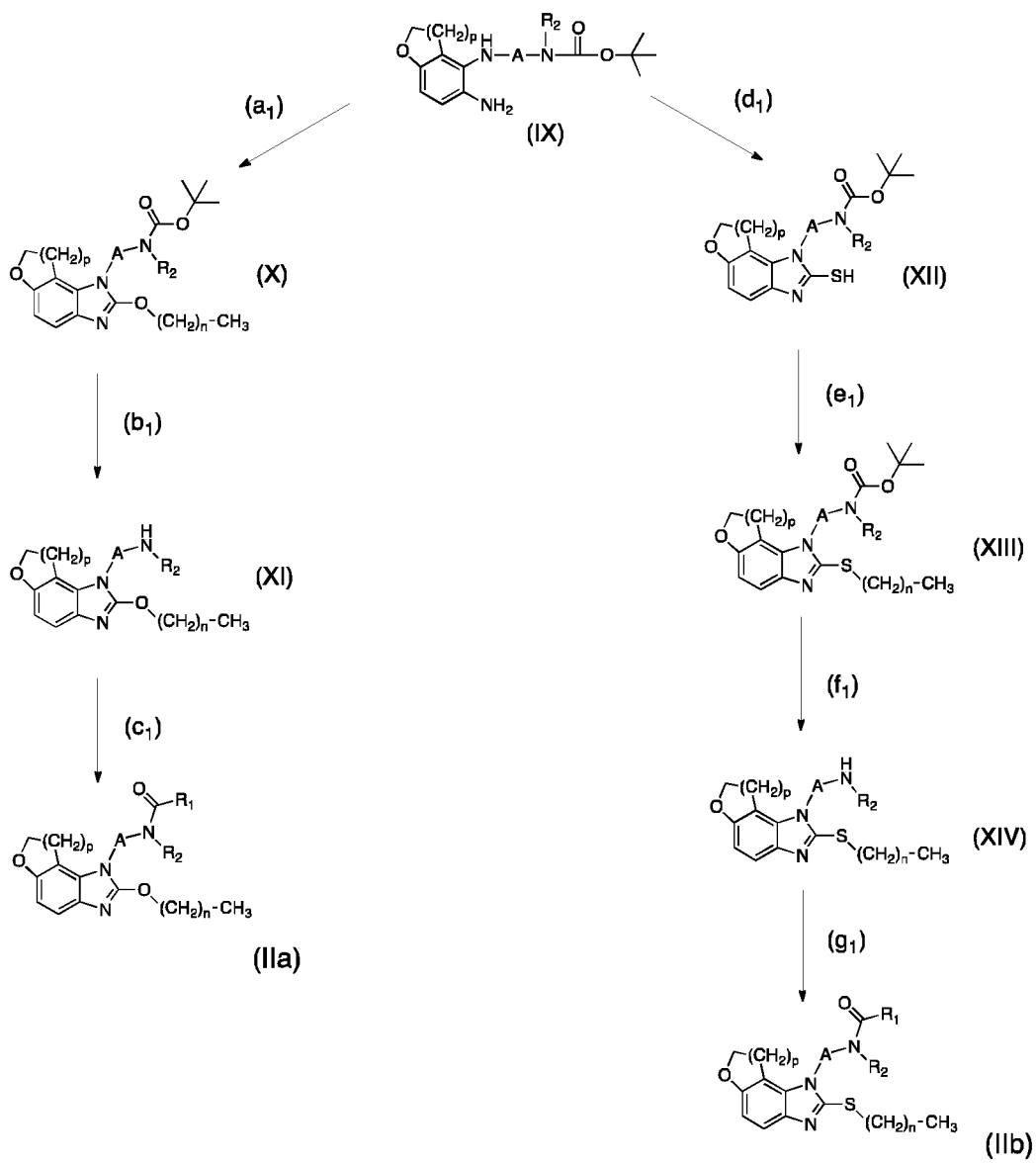

FIG. 3. Example of the process for obtaining the compound of the general formula (II), including compounds of formulae (IIa) and (IIb).

DETAILED DESCRIPTION OF THE INVENTION

The reduced melatonergic activity of benzimidazole analogs previously reported in the literature has been improved in the compounds of the present invention.

This improvement could be explained by the addition of electron withdrawing substituents at the 2-position of the ring, which increases the population of molecules in a non-ionized form and mimics the neutrality of the indole present in the melatonin molecule, a natural agonist of melatonergic receptors.

Affinity differences between indolic and benzimidazole derivatives could be explained by analyzing the stability of the conjugated acids of the benzimidazole system, i.e., by analyzing pKa values and the populations of molecules that are neutral or protonated (positive charge) at pH=7. This is because, in the case of melatonin, a melatonergic agonist with high affinity for MT1 and MT2 receptors, it would be expected that 100% of the population of molecules in solution would be in the neutral form since it is a non-ionizablemolecule at pH=7. In addition, by analyzing the ring structures of other potent agonists of melatonergic receptors MT1 and MT2, such as Ramelteon, one can also observe the majority of the neutral form in these structures. Thus, for benzimidazole derivatives, lower pKa values could better mimic the observed neutrality for melatonin, and consequently have higher affinity for MT1 and MT2 receptors.

If an unsubstituted benzimidazole derivative is protonated (generating its conjugate acid), the entire system delocalizes the electron density through the pi orbitals in order to stabilize the positive charge in the ring. In the case of unsubstituted benzimidazole, this results in a pKa value slightly above 6 (*J. Org. Chem.*, 1961, 26 (8), pp 2789-2791). In other words, a significant population of protonated species with positive formal charge exists at pH=7. However, if the benzimidazole derivative is substituted at the 2-position of the ring with an electron withdrawing group, the substituted derivative would have an electron withdrawal caused by inductive effect in the benzimidazole ring, thus causing a greater destabilization of the protonated form and a greater population of molecules in the neutral form. This factor would lower the pKa value of the benzimidazole derivatives substituted with an electron withdrawing group. Indeed, calculation of the pKa values for the conjugated acids of the benzimidazole ring and its derivative substituted with a methoxy at the 2-position of the ring demonstrated a lower pKa for the latter. The values were obtained using the programs Epik (J. Comput. Aided Mol. Des., 2010, 24, 591-604) and Jaguar (Int. J. Quantum Chem., 2013, 113 (18), 2110-2142), as shown in FIG. 1.

Based on this new and inventive premise of substitution of the benzimidazole nucleus at position 2 to obtain a more acidic molecule for the protonated species, a surprising result of a greater affinity for melatonergic receptors was achieved. A binding of 66% (in MT1) and 52% (in MT2) was observed with the unsubstituted benzimidazole derivative (IA2-116) and 100% (in MT1) and 98% (in MT2) with the 2-methoxy-substituted benzimidazole derivative (IA2-118) (both at the concentration of 1 uM). The binding improvement can be explained since, at neutral pH, there is a larger population of IA2-118 in the neutral form, as well as melatonin.

The benzimidazole compounds of the present invention are represented by the general formula (I)

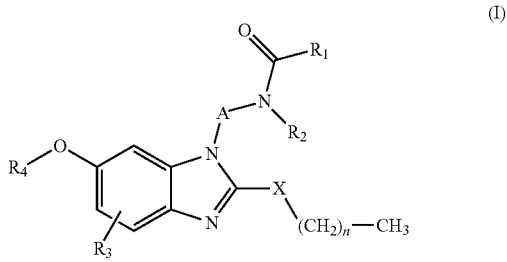

wherein
X is an oxygen or sulfur atom;
A represents a linear C2-4 alkyl group which may have one or more of its hydrogens substituted by an alkyl group selected from methyl, ethyl, propyl or isopropyl;
R1 represents a C1-6 alkyl group, or C2-6 alkenyl, or C2-6 alkynyl, or C1-6 haloalkyl, or C3-6 cycloalkyl, or C1-2 alkyl-C3-6 cycloalkyl;
R2 represents a hydrogen or a C1-3 alkyl group;
R3 represents a hydrogen or a halogen atom;
R4 represents a C1-6 alkyl group,
n is 0 or 1
and by its particular realization where the substituent —O—R4 forms a third cycle through the substitution of a vicinal hydrogen in the benzene ring, which is represented by the general formula (II)

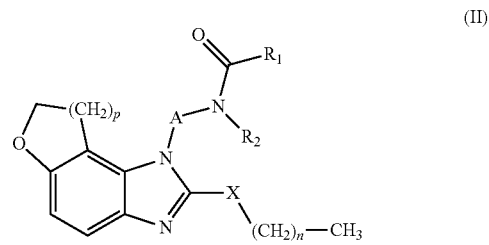

wherein X, R 1, R 2 and "n" are as described for the compound of general formula (I) and "p" represents 1 or 2.

In order to clarify or elucidate the terms used in the present invention and their scope, more detailed definitions of the concepts presented in this document are shown.

In the present invention, unless otherwise defined, the terms alkyl, haloalkyl, cycloalkyl, alkenyl and alkynyl include both branched and unbranched derivatives.

The term alkyl refers to a straight or branched chain hydrocarbon which is fully saturated. Non-limiting examples of alkyls are: methyl, ethyl, propyl, butyl, pentyl, hexyl and isomers thereof.

The terms alkenyl and alkynyl correspond to straight or branched chain hydrocarbons containing unsaturation, alkenyls having at least one double bond and the alkynyls having at least one triple bond. Non-limiting examples of alkenyls and alkynyls are: ethenyl, propenyl, butenyl, pentenyl, hexenyl, ethynyl, propynyl, butynyl, pentynyl, hexynyl and isomers thereof.

The term haloalkyl corresponds to an alkyl group containing at least one of its hydrogens substituted by a halogen selected from the group comprising fluorine, chlorine, bromine and iodine. Non-limiting examples of haloalkyls are:

chloromethyl, chloroethyl, chloropropyl, chlorobutyl, bromomethyl, bromoethyl, bromopropyl, bromobutyl, fluorobutyl, fluoroethyl, fluoropropyl, fluorobutyl, trichloromethyl, trifluoromethyl, tribromomethyl, iodomethyl, iodoethyl, iodopropyl and isomers thereof.

The term cycloalkyl corresponds to fully saturated monocyclic hydrocarbons. Non-limiting examples are cyclopropyl, cyclobutyl, cyclopentyl and cyclohexyl.

The term alkyl-cycloalkyl corresponds to a C3-6 cycloalkyl which is attached to a compound by an alkyl group comprising at least one carbon atom.

The halogens preferably selected for use in the present invention correspond to fluorine, bromine, chlorine and iodine.

All definitions of compounds described herein, in addition to possible variations in their chemical forms, also include their structural and physical modifications, including possible isomers, their polymorphic forms, solvates and hydrates or amorphous form.

In specific cases where the compound of the present invention has asymmetric carbons, pure enantiomers, racemic mixtures thereof and possible diastereomers are included within the scope of the present invention.

In the event that the compound of the present invention shows cis-trans geometric isomerism or E-Z isomerism, it is understood that these independent or associated isomers are within the scope of this invention.

The preferred, but not limited, examples of the compound of general formula (I) include:
N-(2-(2-ethoxy-6-methoxy-1H-benzimidazol-1-yl)ethyl) acetamide;
N-(2-(2-ethoxy-6-methoxy-1H-benzimidazol-1-yl)ethyl) propionamide;
N-(2-(2-ethoxy-6-methoxy-1H-benzimidazol-1-yl)ethyl) butyramide;
N-(2-(2-ethoxy-6-methoxy-1H-benzimidazol-1-yl)ethyl) cyclopropane carboxamide;
N-(2-(2-ethoxy-6-methoxy-1H-benzimidazol-1-yl)ethyl) cyclobutanecarboxamide;
N-(2-(2-ethoxy-6-methoxy-1H-benzimidazol-1-yl)ethyl) cyclopentane carboxamide;
N-(2-(2-ethoxy-6-methoxy-1H-benzimidazol-1-yl)ethyl) cyclohexane carboxamide;
N-(3-(2-ethoxy-6-methoxy-1H-benzimidazol-1-yl)propyl) acetamide;
N-(3-(2,6-dimethoxy-1H-benzimidazol-1-yl)propyl) acetamide;
N-(2-(2,6-dimethoxy-1H-benzimidazol-1-yl)ethyl) acetamide;
N-(2-(2,6-dimethoxy-1H-benzimidazol-1-yl)ethyl)propionamide;
N-(2-(2,6-dimethoxy-1H-benzimidazol-1-yl)ethyl)butyramide;
N-(1-(2-Ethoxy-6-methoxy-1H-benzimidazol-1-yl)propan-2-yl) acetamide;
2-Bromo-N-(2-(2-ethoxy-6-methoxy-1H-benzimidazol-1-yl)ethyl) acetamide;
N-(2-(6-methoxy-2-(methylthio)-1H-benzimidazol-1-yl) ethyl) acetamide;
N-(2-(5-bromo-2-ethoxy-6-methoxy-1H-benzimidazol-1-yl)ethyl) acetamide;
N-(2-(5-chloro-2-ethoxy-6-methoxy-1H-benzimidazol-1-yl)ethyl) acetamide;
N-(3-(5-chloro-2-ethoxy-6-methoxy-1H-benzimidazol-1-yl)propyl) acetamide;
N-(3-(5-chloro-2,6-dimethoxy-1H-benzimidazol-1-yl) propyl) acetamide;
N-(2-(5-chloro-2,6-dimethoxy-1H-benzimidazol-1-yl) ethyl) acetamide;
N-(2-(5-chloro-2-ethoxy-6-methoxy-1H-benzimidazol-1-yl)ethyl)cyclopropane carboxamide;
N-(2-(7-chloro-2-ethoxy-6-methoxy-1H-benzimidazol-1-yl)ethyl) acetamide The preferred, but not limited, examples of the compound of general formula (II) include:
N-(2-(2-ethoxy-7,8-dihydro-1H-benzofuran[4,5-d]imidazol-1-yl)ethyl) acetamide;
N-(2-(2-methoxy-7,8-dihydro-1H-benzofuran[4,5-d]imidazol-1-yl)ethyl)acetamide.

The compounds of general formulae (I) and (II) of the present invention have been synthesized according to FIGS. 2 and 3 shown in the present invention.

According to FIG. 2, the starting compound (III), obtained from a similar procedure to that described by Depreux (*Synthetic Communications* 1994, 24 (15), 2123-2132), is acylated using anhydrides or carboxylic acids halides for the introduction of the R1 substituent, resulting in the intermediate compound (VI). Then, the compound (VI) is reduced to the intermediate (VII). The intermediate (VII) is cyclized using tetraalkyl orthocarbonates, such as tetramethylorthocarbonate and tetraethyl orthocarbonate, resulting in the compound of formula (Ia), wherein the substituent R3 corresponds to a hydrogen. The introduction of the halogen as substituent R3 is performed in a subsequent step, by reacting the compound (Ia) with an N-halosuccinimide selected from the group comprising N-bromosuccinimide, N-chlorosuccinimide and N-iodosuccinimide, resulting in the compound of formula (Ia) wherein R3 is bromide, chlorine or iodine.

Alternatively, the cyclization of intermediate (VII) with thiourea results in the formation of intermediate (VIII), which is alkylated using an alkylating agent for the formation of the compound of formula (Ib) where R3 corresponds to a hydrogen. Similarly, the introduction of the halogen as substituent R3 is performed in a subsequent step by reacting the compound (Ib) with an N-halosuccinimide selected from the group comprising N-bromosuccinimide, N-chlorosuccinimide and N-iodosuccinimide, resulting in the compound of formula (Ib) wherein R3 is bromide, chlorine or iodine.

FIG. 3 describes the obtainment of the compound of general formula (II). According to this diagram, the intermediate (IX), obtained from a similar procedure to that described by Koike et al. (*Journal of Medicinal Chemistry* 2011, 54 (12), 4207-4218), is cyclized using tetraalkylorthocarbonates, such as tetramethylorthocarbonate and tetraethyl orthocarbonate, resulting in the intermediate (X). This intermediate is deprotected to result in the intermediate (XI), which is acylated using carboxylic acid anhydrides or halides for the introduction of the R1 substituent, thereby obtaining the compound of formula (IIa).

Alternatively, cyclization of intermediate (IX) with thiourea results in the formation of intermediate (XII), which is alkylated using an alkylating agent resulting in the intermediate (XIII). Then, the intermediate (XIII) is deprotected and acylated with carboxylic acid anhydrides or halides for the introduction of the R1 substituent, thereby obtaining the compound of formula(IIb).

It is noteworthy that compounds of formulae (Ia) and (Ib) are integral part of the invention and are included in the compound of general formula (I).

Similarly, the compounds of formulae (IIa) and (IIb) are an integral part of the invention and are included in the compound of general formula (II).

Therefore, a further object of the present invention is the process to obtain the compound of general formula (I), comprising the following steps:

(a) reacting of a compound of formula(III)

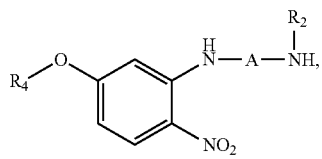
(III)

with a carboxylic acid anhydride of formula(IV)

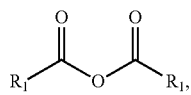
(IV)

or with a carboxylic acid halide of formula(V)

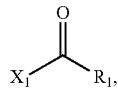
(V)

wherein R1, R2 and R4 are as described for the compound of general formula (I) and X1 corresponds to a halogen selected from the group comprising chlorine and bromine, to obtain a compound of formula (VI)

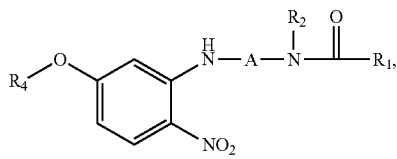
(VI)

(b) reacting of the compound (VI) obtained in step (a) with a reducing agent to obtain the compound of formula (VII)

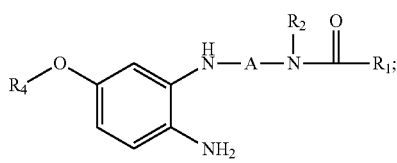
(VII)

(c) reacting of the compound (VII) obtained in step (b) with a tetraalkylorthocarbonate selected from the group comprising tetramethylorthocarbonate and tetraethyl orthocarbonate, to obtain the compound of formula(Ia)

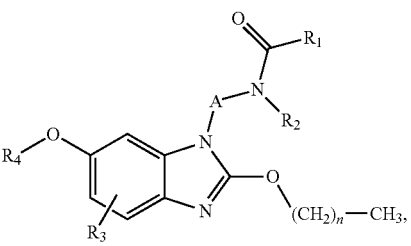
(Ia)

wherein R3 represents a hydrogen atom and "n" represents zero or one;

reacting of the compound of formula (Ia) obtained in step (c) with a halogenating agent selected from the group comprising N-bromosuccinimide, N-chlorosuccinimide and N-iodosuccinimide, to obtain the compound of formula (Ia), wherein R3 represents a halogen selected from the group comprising bromine, chlorine and iodine;

Therefore, a further object of the present invention is the process to obtain the compound of general formula(I), comprising the following steps:

(a) reacting of a compound of general formula (III)

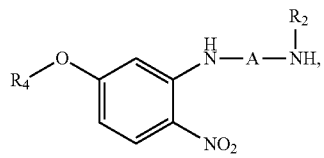
(III)

with a carboxylic acid anhydride of formula(IV)

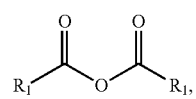
(IV)

or with a carboxylic acid halide of formula(V)

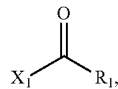
(V)

wherein R1, R2 and R4 are as described for the compound of formula (I) and X1 represents a halogen selected from the group comprising chlorine and bromine, to obtain a compound of formula(VI)

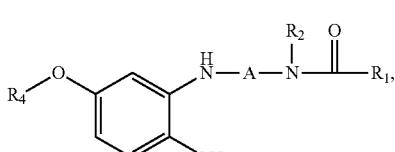
(VI)

(b) reacting of the compound (VI) obtained in step (a) with a reducing agent to obtain the compound of formula(VII)

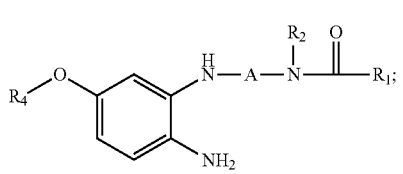

(VII)

(e) reacting of the compound (VII) obtained in step (b) with thiourea in order to obtain the compound (VIII)

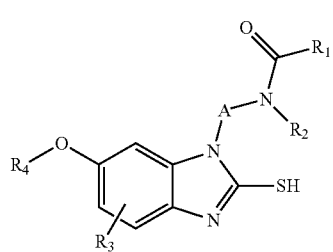

(VIII)

wherein R3 represents a hydrogen atom;
(f) reacting the compound (VIII) obtained in step (e) with an alkylating agent to obtain the compound of formula (Ib)

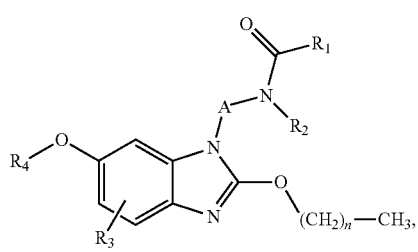

(Ib)

wherein R3 represents a hydrogen atom and "n" corresponds to zero or one;
(g) reacting the compound of formula (Ib) obtained in step (f) with a halogenating agent selected from the group comprising N-bromosuccinimide, N-chlorosuccinimide and N-iodosuccinimide, to obtain the compound of general formula (Ib) wherein R3 represents a halogen selected from the group comprising bromine, chlorine and iodine.

Another object of the present invention is the process to obtain the compound of general formula (II) comprising the following steps:
(a) reacting of a compound of formula(IX):

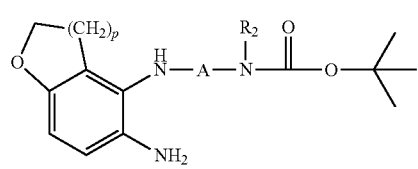

(IX)

with a tetraalkylorthocarbonate selected from the group comprising tetramethylorthocarbonate and tetraethyl orthocarbonate, to obtain a compound of formula (X)

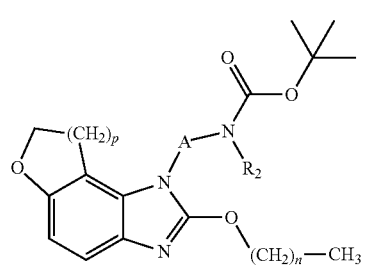

(X)

wherein R2, "n" and "p" are as described for the compound of general formula (II);
(b) reacting the compound of formula (X) obtained in step (a) with a deprotecting agent to obtain a compound of formula (XI):

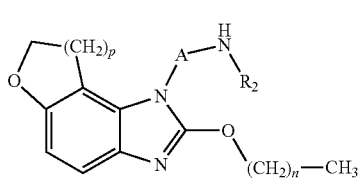

(XI)

(c) reacting of the compound of formula (XI) obtained in (b) with a carboxylic acid anhydride of formula(IV):

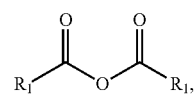

(IV)

or with a carboxylic acid halide of formula(V):

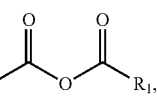

(V)

to obtain the compound of formula(IIa),

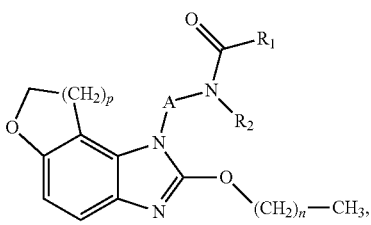

(IIa)

wherein R1 is as described for the compound of formula (I) and X1 represents a bromine or chlorine atom.

In an optional embodiment, the process of obtaining the compound of general formula (II) comprises the following steps:

(d) reacting of a compound of formula (IX)

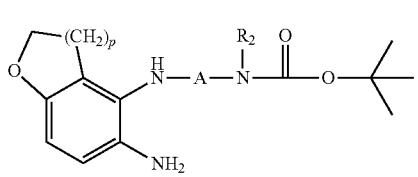

with thiourea resulting in the compound of formula (XII)

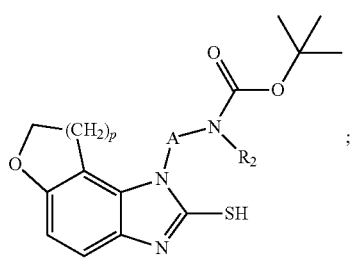

(e) reacting the compound of formula (XII) obtained in step (d) with an alkylating agent resulting in the compound of formula (XIII)

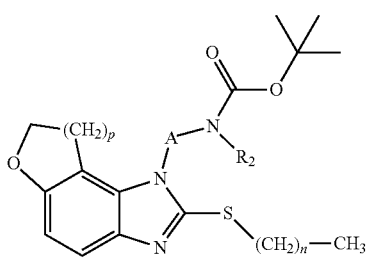

wherein "n" is as described for the compound of formula (I);

(f) reacting the compound obtained in (e) with a deprotecting agent to obtain a compound of formula XIV:

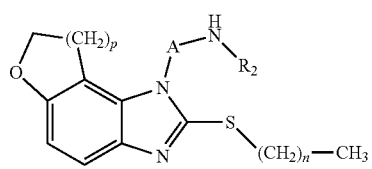

(g) reacting the compound of formula (XIV) obtained in (f) with a carboxylic acid anhydride of formula (IV)

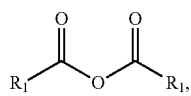

or with a carboxylic acid halide of formula (V)

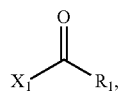

to obtain the compound of formula (IIb):

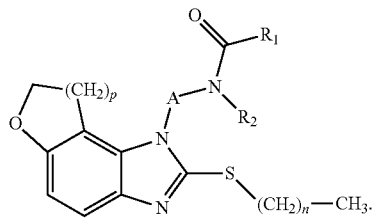

Once again, it is noteworthy that the compounds of formulae (Ia) and (Ib) are an integral part of the invention and are included in the compound of general formula (I). Similarly, the compounds of formulae (IIa) and (IIb) are an integral part of the invention and are included in the compound of formula (II).

The carboxylic acid anhydrides used in the process of obtaining the compound of formulae (I) or (II) comprise commercially available compounds or those synthetically produced. Non-limiting examples of carboxylic acid anhydrides which may be used in this invention include acetic, propionic, butyric, crotonic, valeric anhydrides, among others.

The carboxylic acid halides employed in the process of obtaining the compound of formula (I) or (II), comprise both the commercially available and the synthetically prepared compounds. Non-limiting examples of carboxylic acid halides include the chlorides and bromides of acetic, propanoic, butanoic, valeric, cyclopropanecarboxylic, cyclobutanecarboxylic, cyclopentanecarboxylic, cyclohexanecarboxylic, alpha-bromoacetic, alpha-chloroacetic acids, among others.

Alkylating agents are substances that transfer alkyl groups between molecules. There are several alkylating agents available in the market, as well as a variety of reactions used for this purpose. Non-limiting examples of alkylating agents used in the process described in this invention correspond to alkyl halides, such as methyl and ethyl bromides or iodides.

Deprotection agents are chemicals used to remove protecting groups. Protecting groups, in turn, are chemical groups used to protect specific functions which, when unmodified, are likely to react or undergo alteration with reagents used for structural modifications directed to other positions of the molecule. In the present invention a non-limiting example of deprotection agent capable of removing the tert-butoxycarbonyl protecting group from the intermediates (X) and (XIII) corresponds to trifluoroacetic acid.

In the present invention, a reducing agent has the role of promoting the transformation of an aromatic nitro group into an amino group. Several reagents may be used to promote this reduction. Non-limiting examples of typical reducing agents of aromatic nitro groups include iron or tin in hydrochloric acid medium, zinc, several metal catalysts, among others.

It is noteworthy that the present invention also comprises isomers, tautomers, pure enantiomers, racemic mixtures and diastereomers of the compound of general formulae (I) or (II), as well as mixtures thereof at any ratios.

Depending on the medium used for crystallization, the compound of formulae (I) or (II) may show different aspects. Thus, the present invention also comprises the amorphous form, the solvates, hydrates and polymorphs of the compound of formulae (I) or (II).

In order to exert its activity, the compound of formulae (I) or (II) should be administered to an animal, mammal, particularly a human, preferably as a pharmaceutical composition, i.e., associated o pharmaceutically acceptable vehicles which are acceptable to each route of administration.

The pharmaceutical compositions of the present invention contain one or more compounds herein proposed, as active ingredient, associated with one or more pharmaceutically acceptable vehicles. The active ingredient is commonly mixed, diluted or encapsulated with at least one vehicle. The final composition may be a capsule, sachet, paper or other way of containment. When the vehicle is a diluent, it may be in solid, semi-solid, or liquid form, acting as a carrier, excipient or medium for the active ingredient. Thus, the composition may be tablets, pills, powders, sachets, suspensions, emulsions, solutions, aerosols (in solid or liquid medium), creams, hard or soft capsules, suppositories, injections.

In the present invention, it is considered a pharmaceutically acceptable vehicle any substance other than the compound of general formulae (I) or (II), which has been intentionally added thereto to produce a pharmaceutical dosage form suitable to a route of administration. Non-limiting examples of pharmaceutical acceptable vehicle (excipients) suitable for pharmaceutical compositions are described in *Handbook of Pharmaceutical Manufacturing Formulations*—Vol. 1 to 6-2004—Sarfaraz K. Niazi—CRC-Press and Remington's Pharmaceutical Sciences, Mack Publishing.

Non-limiting examples of routes of administration of the composition comprising the compound of general formulae (I) or (II) are oral, parenteral, nasal, rectal, transmucosal and transdermal routes, oral administration being particularly preferred.

The therapeutic dose to be used with respect to the compounds of the present invention should be planned and calculated according to route of administration chosen, age, weight and condition of the patient and disorder severity. Overall, the compounds of the present invention are administered in therapeutically effective doses ranging from about 0.1 mg to about 2,000 mg per day. Effective doses may be extrapolated from dose-response curves obtained from in vitro or animal models. Typically, the physician will administer the compound to a suitable dose in order to achieve the expected effect.

The examples described in the experimental section are intended to exemplify one of the several ways of carrying out the invention, but without limiting the scope thereof.

Example 1

N-(2-(2-ethoxy-6-methoxy-1H-benzimidazol-1-yl)ethyl)acetamide

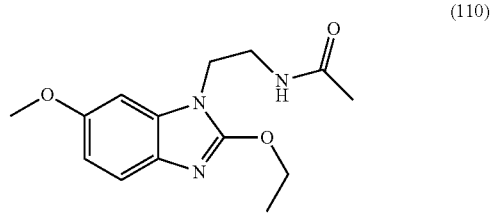 [SMILES: CCOc1nc2ccc(OC)cc2n1CCNC(C)=O]

(110)

(A) N-(2-((5-methoxy-2-nitrophenyl)amino)ethyl)acetamide

In a 500 ml reactor equipped with reflux condenser, magnetic stirring and heating, $N^1$-(5-methoxy-2-nitrophenyl)ethane-1,2-diamine (6.0 g, 28.4 mmol) (Depreux Et al., *Synthetic Communications* 1994, col. 24 (15), pp. 2123-2132), ethanol (200 ml) and acetic anhydride (2.78 ml, 29.2 mmol) were added. The reaction medium was heated to a temperature of 60° C. and kept under stirring for 1 hour to complete the reaction. The ethanol was roto-evaporated to dryness and the residue dissolved in chloroform (400 ml). The chloroform solution was washed with 15% aqueous sodium carbonate solution (2×200 ml). The organic phase was separated, dried with magnesium sulfate and roto-evaporated to yield the title compound as a yellow solid which was used directly in the next step. (m=6.8 g. Yield: 94.5%)

(B) N-(2-((2-amino-5-methoxyphenyl)amino)ethyl)acetamide

In a 500 ml reactor, N-(2-((5-methoxy-2-nitrophenyl)amino)ethyl)acetamide (3.0 g, 11.8 mmol) and methanol (300 ml) were added. The mixture was heated to a temperature of approximately 45° C. under stirring to dissolve the solid. Then the solution was cooled to room temperature and zinc powder (11.55 g, 176 mmol) and ammonium formate (5.61 g, 89.0 mmol) were added under vigorous stirring. The mixture was kept under stirring for approximately 1 hour and then gravity filtered. The filtrate was roto-evaporated and the residue was extracted with dichloromethane (3×300 ml). The combined organics were washed with 6M aqueous sodium hydroxide solution (2×500 ml), followed by saturated sodium chloride solution (400 ml). The organic phase was separated, dried with magnesium sulfate and roto-evaporated yielding oil, which was used directly in the next step. (m=2.4 g. Yield: 91%)

(C) N-(2-(2-ethoxy-6-methoxy-1H-benzimidazol-1-yl)ethyl)acetamide

In a 50 ml reactor containing N-(2-((2-amino-5-methoxyphenyl)amino)ethyl)acetamide (500 mg, 2.24 mmol), were added tetraethyl orthocarbonate (1.72 g, 8.96 mmol) and subsequently acetic acid (0.013 g, 0.216 mmol). The reaction was heated to 80° C. and kept at this temperature for 30 min. Then the reaction medium was allowed to return to room temperature and ethyl ether (25 ml) was added. The precipitated solid was filtered, washed with ethyl ether (25 ml) and purified by MPLC (CHCl3:MeOH 9:1) resulting in a white solid product. (m=385 mg. Yield: 62%)

$^1$H NMR (300 MHz, CHLOROFORM-d) δ ppm 1.45 (t, J=7.08 Hz, 4H) 1.92 (s, 3H) 3.58 (q, J=5.89 Hz, 3H) 3.83 (s, 3H) 4.06-4.15 (m, 3H) 4.51 (q, J=7.08 Hz, 2H) 5.77 (br s, 1H) 6.72 (s, 1H) 6.75-6.80 (m, 1H) 7.40 (d, J=8.57 Hz, 1H);

$^{13}$C NMR (75 MHz, CHLOROFORM-d) δ ppm 14.71 (s, 1C) 23.10 (s, 1 C) 38.99 (s, 1C) 41.23 (s, 1C) 56.01 (s, 1C) 66.12 (s, 1C) 93.51 (s, 1C) 109.24 (s, 1C) 118.07 (s, 1C) 134.05 (s, 1C) 134.35 (s, 1C) 155.55 (s, 1C) 156.78 (s, 1C) 170.53 (S, 1C).

Example 2

N-(2-(2-ethoxy-6-methoxy-1H-benzimidazol-1-yl)ethyl)propionamide

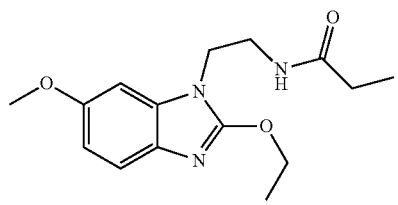

(112)

(A) N-(2-((5-methoxy-2-nitrophenyl)amino)ethyl)propionamide

In a 100 ml reactor with magnetic stirring, N1-(5-methoxy-2-nitrophenyl)ethane-1,2-diamine(1 g, 4.73 mmol), dichloromethane (50 ml) and triethylamine (0.67 ml, 4.81 mmol) were added. The reaction medium was kept under stirring and a solution of propionyl chloride (0.42 ml, 4.80 mmol) in dichloromethane (10 ml) was slowly added through an addition funnel. The reaction medium was kept under stirring at room temperature for 2 hours. After the completion of the reaction, 20 ml of 10% aqueous hydrochloric acid solution (20 ml) were added. The dichloromethane was separated and the aqueous phase extracted with dichloromethane (2×20 ml). The organic phase was washed with 5% aqueous bicarbonate solution (100 ml) and saturated sodium chloride solution (100 ml). The organic extract was separated, dried with anhydrous magnesium sulfate and roto-evaporated, yielding a yellow solid product which was used directly in the next step. (m=1.14 g. Yield: 90%)

(B) N-(2-((2-amino-5-methoxyphenyl)amino)ethyl)propionamide

N-(2-((5-methoxy-2-nitrophenyl)amino)ethyl)propionamide (0.56 g, 2.10 mmol) and methanol (50 ml) were added to a 100 ml reactor. The mixture was heated to a temperature of approximately 45° C. under stirring to dissolve the solid. Then the solution was cooled to room temperature and zinc powder (2.04 g, 31.2 mmol) and ammonium formate (0.99 g, 15.7 mmol) were added under vigorous stirring. The mixture was kept under stirring for approximately 1 hour and then gravity filtered. The filtrate was roto-evaporated and dichloromethane (300 ml) was added to the residue. The mixture was kept under stirring to extract the product, filtered, washed with 6M aqueous sodium hydroxide solution (2×200 ml), followed by saturated sodium chloride solution (300 ml). The organic phase was separated, dried with magnesium sulfate and roto-evaporated to dryness yielding oil, which was used directly in the next synthetic step. (m=0.45 g. Yield: 90%)

(C) N-(2-(2-ethoxy-6-methoxy-1H-benzimidazol-1-yl)ethyl) propionamide

In a 50 ml reactor containing N-(2-((2-amino-5-methoxyphenyl)amino)ethyl)propionamide (450 mg, 1.90 mmol), tetraethyl orthocarbonate (1.46 g, 7.59 mmol) and subsequently acetic acid (0.011 g, 0.189 mmol) were added. The reaction was heated to 80° C. and kept at this temperature for 30 min. Then the reaction medium was allowed to return to room temperature and ethyl ether (25 ml) was added. The precipitated solid was filtered, washed with ethyl ether (25 ml) and purified by MPLC (CHCl3:MeOH 9:1) resulting in a white solid product. (m=309 mg. Yield: 56%)

$^1$H NMR (500 MHz, CHLOROFORM-d) δ ppm 1.18-1.35 (m, 4H) 1.46 (t, J=7.10 Hz, 2H) 2.13 (q, J=7.55 Hz, 1H) 3.59 (q, J=5.89 Hz, 1H) 3.77-3.84 (m, 2H) 4.11 (t, J=5.76 Hz, 1H) 4.55 (q, J=7.15 Hz, 1H) 5.64 (br s, 1H) 6.77 (dd, J=8.64, 2.48 Hz, 1H) 7.26 (s, 1H) 7.40 (d, J=8.64 Hz, 1H)

Example 3

N-(2-(2-ethoxy-6-methoxy-1H-benzimidazol-1-yl)ethyl)butyramide

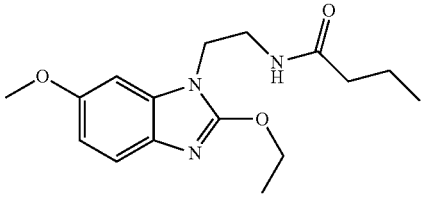

(113)

(A) N-(2-((5-methoxy-2-nitrophenyl)amino)ethyl)butyramide

In a 100 ml reactor with magnetic stirring, N1-(5-methoxy-2-nitrophenyl)ethane-1,2-diamine (1 g, 4.73 mmol), dichloromethane (50 ml) and triethylamine (0.67 ml, 4.80 mmol) were added. The reaction medium was kept under stirring and a solution of butanoyl chloride (0.49 ml, 4.73 mmol) in dichloromethane (10 ml) was slowly added through an addition funnel. The reaction medium was kept under stirring at room temperature for 2 hours. After the completion of the reaction, 10% aqueous hydrochloric acid solution (10 ml) was added. The dichloromethane was separated and the aqueous phase extracted with dichloromethane (2×20 ml). The organic phase was washed with 5% aqueous bicarbonate solution (100 ml) and saturated sodium chloride solution (100 ml). The organic extract was separated, dried with anhydrous magnesium sulfate and roto-evaporated, yielding a yellow solid product which was used directly in the next step. (m=1.17 g. Yield: 88%)

(B) N-(2-((2-amino-5-methoxyphenyl)amino)ethyl)butyramide

N-(2-((5-methoxy-2-nitrophenyl)amino)ethyl) butyramide (0.51 g, 1.81 mmol) and methanol (50 ml) were added to a 100 ml reactor. The mixture was heated to a temperature of approximately 45° C. under stirring to dissolve the solid. Then the solution was cooled to room temperature and powdered zinc (1.76 g, 26.9 mmol) and ammonium formate (0.86 g, 13.6 mmol) were added under vigorous stirring. The mixture was kept under stirring for approximately 1 hour and then gravity filtered. The filtrate was roto-evaporated, the residue extracted with dichloromethane (300 ml), washed with 6M aqueous sodium hydroxide solution (2×200 ml), followed by saturated aqueous sodium chloride solution (300 ml). The organic phase was separated, dried with magnesium sulfate and roto-evaporated to dryness yielding oil, which was used directly in the next step of synthesis. (m=0.40 g. Yield: 87.8%)

(C) N-(2-(2-ethoxy-6-methoxy-1H-benzimidazol-1-yl)ethyl) butyramide

In a 50 ml reactor containing N-(2-((2-amino-5-methoxyphenyl)amino)ethyl)butyramide (400 mg, 1.59 mmol) tetraethyl orthocarbonate (1.22 g, 6.37 mmol) and subsequently acetic acid (0.010 g, 0.159 mmol) were added. The reaction was heated to 80° C. and kept at this temperature for 30 min. Then the reaction medium was allowed to return to room temperature and ethyl ether (20 ml) was added. The precipitated solid was filtered, washed with ethyl ether (20 ml) and purified by MPLC (CHCl3:MeOH 9:1) resulting in a white solid product. (m=258 mg. Yield: 53%)

¹H NMR (500 MHz, CHLOROFORM-d) δ ppm 0.91 (t, J=7.38 Hz, 3H) 1.46 (t, J=7.08 Hz, 3H) 1.57-1.67 (m, 3H) 2.05-2.10 (m, 2H) 3.60 (q, J=5.97 Hz, 2H) 3.81-3.86 (m, 3H) 4.08-4.14 (m, 2H) 4.54 (q, J=7.13 Hz, 2H) 5.64 (br s, 1H) 6.72 (s, 1H) 6.76-6.79 (m, 1H) 7.26 (s, 1H) 7.40 (d, J=8.61 Hz, 1H)

Example 4

N-(2-(2-ethoxy-6-methoxy-1H-benzimidazol-1-yl)ethyl)cyclopropane carboxamide

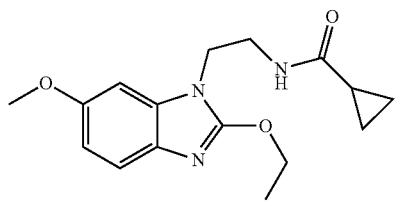

(125)

(A) N-(2-((5-methoxy-2-nitrophenyl)amino)ethyl)cyclopropanecarboxamide

In a 100 ml reactor with magnetic stirring, N1-(5-methoxy-2-nitrophenyl) ethane-1,2-diamine (1 g, 4.73 mmol), dichloromethane (50 ml) and triethylamine (0.67 ml, 4.80 mmol) were added. The reaction medium was kept under stirring and a solution of cyclopropanecarbonyl chloride (0.43 ml, 4.73 mmol) in dichloromethane (10 ml) was slowly added through an addition funnel. The reaction medium was kept under stirring at room temperature for 2 hours. After the completion of the reaction, 10% aqueous hydrochloric acid solution (10 ml) was added. The dichloromethane was separated and the aqueous phase extracted with dichloromethane (2×20 ml). The organic phase was washed with 5% aqueous bicarbonate solution (100 ml) and saturated sodium chloride solution (100 ml). The organic extract was separated, dried with anhydrous magnesium sulfate and roto-evaporated, yielding a yellow solid product which was used directly in the next step. (m=1.17 g. Yield: 88.5%)

(B) N-(2-((2-amino-5-methoxyphenyl)amino)ethyl) cyclopropane carboxamide

In a 200 ml reactor, N-(2-((5-methoxy-2-nitrophenyl)amino)ethyl)cyclopropane carboxamide (0.79 g, 2.83 mmol) and methanol (70 ml) were added. The mixture was heated to a temperature of approximately 45° C. under stirring to dissolve the solid. Then the solution was cooled to room temperature and powdered zinc (2.78 g, 42.5 mmol) and ammonium formate (1.34, 22.3 mmol) were added under vigorous stirring. The mixture was kept under stirring for approximately 1 hour and then gravity filtered. The filtrate was roto-evaporated and dichloromethane (300 ml) was added to the residue. The mixture was kept under stirring to extract the product, filtered, washed with 6M aqueous sodium hydroxide solution (2×150 ml), followed by saturated sodium chloride solution (150 ml). The organic phase was separated, dried with magnesium sulfate and roto-evaporated to dryness yielding oil, which was used directly in the next step of synthesis. (m=0.64 g. Yield: 90.8%)

(C) N-(2-(2-ethoxy-6-methoxy-1H-benzimidazol-1-yl)ethyl) cyclopropane carboxamide In a 50 ml reactor containing N-(2-((2-amino-5-methoxyphenyl)amino)ethyl)cyclopropane carboxamide (500 mg, 2.01 mmol), tetraethyl orthocarbonate (1.54 g, 8.01 mmol) and subsequently acetic acid (0.012 g, 0.201 mmol) were added. The reaction was heated to 80° C. and kept at this temperature for 30 min. Then the reaction medium was allowed to return to room temperature and ethyl ether (25 ml) was added. The precipitated solid was filtered, washed with ethyl ether (25 ml) and purified by MPLC (CHCl3:MeOH 9:1) resulting in a white solid product. (m=350 mg. Yield: 57.5%)

¹H NMR (500 MHz, CHLOROFORM-d) δ ppm 0.67-0.77 (m, 2H) 0.80-1.03 (m, 2H) 1.19-1.34 (m, 1H) 1.45 (t, J=7.10 Hz, 3H) 3.61 (q, J=5.95 Hz, 2H) 3.83 (s, 3H) 4.10 (t, J=5.65 Hz, 2H) 4.51 (q, J=7.02 Hz, 2H) 5.96 (br s, 1H) 6.71 (d, J=2.29 Hz, 1H) 6.78 (dd, J=8.70, 2.44 Hz, 1H) 7.40 (d, J=8.54 Hz, 1H)

Example 5

N-(2-(2-ethoxy-6-methoxy-1H-benzimidazol-1-yl) ethyl) cyclobutanecarboxamide

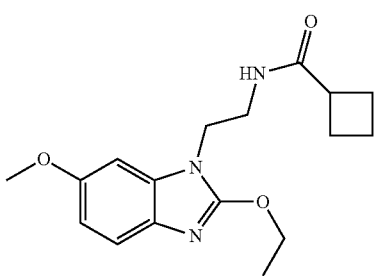

(126)

(A) N-(2-((5-methoxy-2-nitrophenyl)amino)ethyl) cyclobutanecarboxamide

In a 100 ml reactor with magnetic stirring, N1-(5-methoxy-2-nitrophenyl)ethane-1,2-diamine (1 g, 4.73 mmol), dichloromethane (50 ml) and triethylamine (0.67 ml, 4.80 mmol) were added. The reaction medium was kept under stirring and a solution of cyclobutanecarbonyl chloride (0.54 ml, 4.73 mmol) in dichloromethane (10 ml) was slowly added through an addition funnel. The reaction medium was kept under stirring at room temperature for 2 hours. After the completion of the reaction, 10% aqueous hydrochloric acid solution (10 ml) was added. The dichloromethane was separated and the aqueous phase was extracted with dichloromethane (2×20 ml). The organic phase was washed with 5% aqueous bicarbonate solution (100 ml) and saturated sodium chloride solution (100 ml). The organic extract was separated, dried with anhydrous magnesium sulfate and roto-evaporated, yielding a yellow solid product which was used directly in the next step. (m=1.25 g. Yield: 90%)

(B) N-(2-((2-amino-5-methoxyphenyl)amino)ethyl) cyclobutanecarboxamide

In a 200 ml reactor N-(2-((5-methoxy-2-nitrophenyl)amino)ethyl)cyclobutanecarboxamide (0.785 g, 2.68 mmol) and methanol (60 ml) were added. The mixture was heated to a temperature of approximately 45° C. under stirring to dissolve the solid. Then the solution was cooled to room temperature and 2.60 g of powdered zinc (2.60 g, 39.8 mmol) and 1.26 g of ammonium formate (1.26 g, 20.0 mmol) were added under vigorous stirring. The mixture was kept under stirring for approximately 1 hour and then gravity filtered. The filtrate was roto-evaporated and dichloromethane (300 ml) was added to the residue. The mixture was kept under stirring to extract the product, filtered, washed with 6M aqueous sodium hydroxide solution (2×150 ml), followed by saturated sodium chloride solution (150 ml). The organic phase was separated, dried with magnesium sulfate and roto-evaporated to dryness yielding oil, which was used directly in the next step of synthesis. (m=0.64 g. Yield: 90.8%)

(C) N-(2-(2-ethoxy-6-methoxy-1H-benzimidazol-1-yl)ethyl)cyclobutanecarboxamide In a 50 ml reactor containing N-(2-((2-amino-5-methoxyphenyl)amino)ethyl)cyclobutanecarboxamide (600 mg, 2.28 mmol), tetraethyl orthocarbonate (1.75 g, 9.11 mmol) and subsequently acetic acid (0.014 g, 0.23 mmol) were added. The reaction was heated to 80° C. and kept at this temperature for 30 min. Then the reaction medium was allowed to return to room temperature and ethyl ether (30 ml) was added. The precipitated solid was filtered, washed with ethyl ether (30 ml) and purified by MPLC (CHCl3:MeOH 9:1) resulting in a white solid product. (m=362 mg. Yield: 50%)

$^1$H NMR (500 MHz, CHLOROFORM-d) δ ppm 1.47 (t, J=7.10 Hz, 3H) 1.77-1.97 (m, 2H) 2.04-2.11 (m, 2H) 2.17-2.25 (m, 2H) 2.85-2.92 (m, 1H) 3.60 (q, J=5.95 Hz, 2H) 3.83 (s, 3H) 4.11 (t, J=5.80 Hz, 2H) 4.55 (q, J=7.17 Hz, 2H) 5.54 (br s, 1H) 6.71 (d, J=2.29 Hz, 1H) 6.78 (dd, J=8.70, 2.44 Hz, 1H) 7.41 (d, J=8.70 Hz, 1H)

Example 6

N-(2-(2-ethoxy-6-methoxy-1H-benzimidazol-1-yl)ethyl)cyclopentane carboxamide

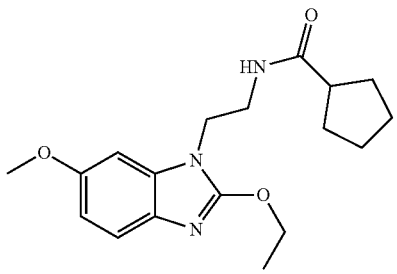

(128)

(A) N-(2-((5-methoxy-2-nitrophenyl)amino)ethyl) cyclopentane carboxamide

N1-(5-methoxy-2-nitrophenyl)ethane-1,2-diamine (1 g, 4.73 mmol), dichloromethane (50 ml) and triethylamine (0.67 ml, 4.80 mmol) were added to a 100 ml reactor with magnetic stirring. The reaction medium was kept under stirring and a solution of cyclopentanecarbonyl chloride (0.585 ml, 4.73 mmol) in dichloromethane (10 ml) was slowly added through an addition funnel. The reaction medium was kept under stirring at room temperature for 2 hours. After the completion of the reaction, 10% aqueous hydrochloric acid solution (10 ml) was added. The dichloromethane was separated and the aqueous phase extracted with dichloromethane (2×20 ml). The organic phase was washed with 5% aqueous bicarbonate solution (100 ml) and saturated sodium chloride solution (100 ml). The organic extract was separated, dried with anhydrous magnesium sulfate and roto-evaporated, yielding a yellow solid product which was used directly in the next step. (m=1.2 g. Yield: 83%)

(B) N-(2-((2-amino-5-methoxyphenyl)amino)ethyl) cyclopentane carboxamide

In a 50 ml reactor N-(2-((5-methoxy-2-nitrophenyl)amino)ethyl)cyclopentane carboxamide (0.100 g, 0.325 mmol) and methanol (20 ml) were added. The mixture was heated to a temperature of approximately 45° C. under stirring to dissolve the solid. Then the solution was cooled to room temperature and zinc powder (0.317 g, 4.85 mmol) and ammonium formate (0.153 g, 2.43 mmol) were added under vigorous stirring. The mixture was kept under stirring for approximately 1 hour and then gravity filtered. The filtrate was roto-evaporated and dichloromethane (100 ml) was added to the residue. The mixture was kept under stirring to extract the product, filtered, washed with 6M aqueous sodium hydroxide solution (2×50 ml), followed by saturated sodium chloride solution (50 ml). The organic phase was separated, dried with magnesium sulfate and roto-evaporated to dryness yielding oil, which was used directly in the next step of synthesis. (m=0.082 g. Yield: 90.8%)

(C) N-(2-(2-ethoxy-6-methoxy-1H-benzimidazol-1-yl)ethyl)cyclopentane carboxamide In a 10 ml reactor containing N-(2-((2-amino-5-methoxyphenyl)amino)ethyl)cyclopentane carboxamide (82 mg, 0.296 mmol), tetraethyl orthocarbonate (0.227 g, 1.18 mmol) and subsequently acetic acid (0.0018 g, 0.030 mmol) were added. The reaction was heated to 80° C. and kept at this temperature for 30 min. Then the reaction medium was allowed to return to room temperature and ethyl ether (5 ml) was added. The precipitated solid was filtered, washed with ethyl ether (5 ml) and purified by MPLC (CHCl3:MeOH 9:1) resulting in a white solid product. (m=49 mg. Yield: 50%).

$^1$H NMR (500 MHz, CHLOROFORM-d) δ ppm 1.41-1.60 (m, 6H) 1.63-1.83 (m, 9H) 2.35-2.44 (m, 1H) 3.60 (q, J=5.85 Hz, 2H) 3.82 (s, 3H) 4.10 (t, J=5.80 Hz, 2H) 4.54 (q, J=7.17 Hz, 2H) 5.62 (br s, 1H) 6.71 (d, J=2.29 Hz, 1H) 6.77 (dd, J=8.54, 2.44 Hz, 1H) 7.40 (d, J=8.70 Hz, 1H)

Example 7

N-(2-(2-ethoxy-6-methoxy-1H-benzimidazol-1-yl)ethyl)cyclohexane carboxamide

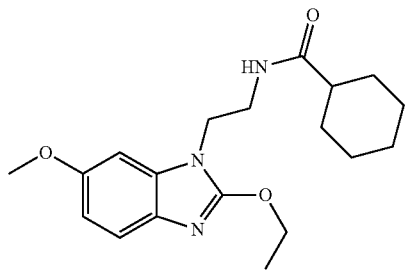

(129)

(A) N-(2-((5-methoxy-2-nitrophenyl)amino)ethyl) cyclohexane carboxamide

N1-(5-methoxy-2-nitrophenyl)ethane-1,2-diamine (1 g, 4.73 mmol), dichloromethane (50 ml) and triethylamine (0.67 ml, 4.80 mmol) were added to a 100 ml reactor with magnetic stirring. The reaction medium was kept under stirring and a solution of 0.64 ml of cyclohexanecarbonyl chloride (0.64 ml, 4.73 mmol) in dichloromethane (10 ml) was slowly added through an addition funnel. The reaction medium was kept under stirring at room temperature for 2 hours. After the completion of the reaction, 10% aqueous hydrochloric acid solution (10 ml) was added. The dichloromethane was separated and the aqueous phase extracted with dichloromethane (2×20 ml). The organic phase was washed with 5% aqueous bicarbonate solution (100 ml) and saturated sodium chloride solution (100 ml). The organic extract was separated, dried with anhydrous magnesium sulfate and roto-evaporated, yielding a yellow solid product which was used directly in the next step. (m=1.3 g. Yield: 86%)

(B) N-(2-((2-amino-5-methoxyphenyl)amino)ethyl) cyclohexane carboxamide

In a 50 ml reactor, 0.100 g of N-(2-((5-methoxy-2-nitrophenyl)amino)ethyl)cyclohexane carboxamide (0.100 g, 0.311 mmol) and methanol (20 ml) were added. The mixture was heated to a temperature of approximately 45° C. under stirring to dissolve the solid. Then the solution was cooled to room temperature and powdered zinc (0.030 g, 4.65 mmol) and ammonium formate (0.147 g, 2.33 mmol) were added under vigorous stirring. The mixture was kept under stirring for approximately 1 hour and then gravity filtered. The filtrate was roto-evaporated and dichloromethane (100 ml) was added to the residue. The mixture was kept under stirring to extract the product, filtered, washed with 6M aqueous sodium hydroxide solution (2×50 ml), followed by saturated sodium chloride solution (50 ml). The organic phase was separated, dried with magnesium sulfate and roto-evaporated to dryness yielding oil, which was employed directly in the next step of synthesis. (m=0.082 g. Yield: 90%)

(C) N-(2-(2-ethoxy-6-methoxy-1H-benzimidazol-1-yl)ethyl)cyclohexane carboxamide

In a 10 ml reactor containing N-(2-((2-amino-5-methoxyphenyl)amino)ethyl)cyclohexane carboxamide (82 mg, 0.281 mmol), tetraethyl orthocarbonate (0.216 g, 0.113 mmol) and subsequently acetic acid (0.0017 g, 0.028 mmol) were added. The reaction was heated to 80° C. and kept at this temperature for 30 min. Then the reaction medium was allowed to return to room temperature and ethyl ether (5 ml) was added. The precipitated solid was filtered, washed with ethyl ether (5 ml) and purified by MPLC (CHCl3:MeOH 9:1) resulting in a white solid product. (m=53.4 mg. Yield: 55%)

$^1$H NMR (500 MHz, CHLOROFORM-d) δ ppm 1.28-1.48 (m, 5H) 1.57-1.68 (m, 4H) 1.69-1.79 (m, 4H) 1.97 (tt, J=11.73, 3.30 Hz, 1H) 3.60 (q, J=5.95 Hz, 2H) 3.83 (s, 3H) 4.10 (t, J=5.72 Hz, 2H) 4.55 (q, J=7.17 Hz, 2H) 6.71 (d, J=2.29 Hz, 1H) 6.77 (dd, J=8.70, 2.44 Hz, 1H) 7.41 (d, J=8.70 Hz, 1H)

Example 8

N-(3-(2-ethoxy-6-methoxy-1H-benzimidazol-1-yl)propyl) acetamide

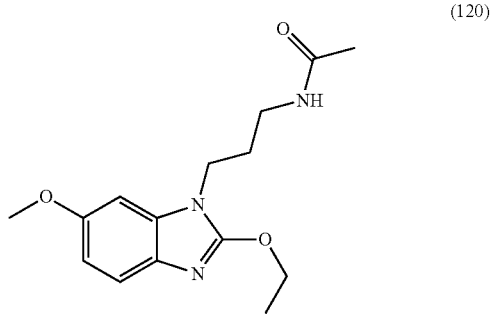 [SMILES: CCOc1nc2ccc(OC)cc2n1CCCNC(C)=O]

(120)

(A) N-(3-((5-methoxy-2-nitrophenyl)amino)propyl) acetamide

In a 100 ml reactor, 3-chloro-4-nitroanisole (7.00 g, 37.3 mmol), 1,3-propylene diamine (37 ml, 439 mmol) and cupric bromide (3.5 g, 15.7 mmol) were added. The reaction medium was kept under stirring and heating at 60-65° C. for 4 hours. After cooling, the reaction medium was diluted with water (140 ml) and extracted with chloroform (3×220 ml). The organic phases were combined and washed with water (300 ml). The chloroform was dried over magnesium sulfate and roto-evaporated to dryness yielding oil, which was dissolved in ethanol (300 ml). To this solution was added acetic anhydride (4.2 ml, 44.1 mmol), the reaction medium was heated to 60° C. and kept under stirring for 1 hour. Then the ethanol was roto-evaporated to dryness and the resulting oil dissolved in ethyl acetate. This solution was washed with 15% aqueous sodium carbonate solution, the acetate phase separated, dried with anhydrous magnesium sulfate and roto-evaporated to yield a yellow oil product which was used directly in the next step. (m=8.2 g. Yield: 82%)

(B) N-(3-((2-amino-5-methoxyphenyl)amino)propyl)acetamide

In a 200 ml reactor, N-(3-((5-methoxy-2-nitrophenyl) amino)propyl)acetamide (1.0 g, 3.74 mmol) and methanol (50 ml) were added. The mixture was kept under vigorous stirring and powdered zinc (3.65 g, 55.8 mmol) and ammonium formate (1.77 g, 28.1 mmol) were added. The mixture was kept under stirring for approximately 1 hour and then gravity filtered. The filtrate was roto-evaporated and dichloromethane (300 ml) was added to the residue. The mixture was kept under stirring to extract the product, filtered, dichloromethane was washed with 6M aqueous sodium hydroxide solution (2×150 ml), followed by saturated sodium chloride solution (150 ml). The organic phase was separated, dried with magnesium sulfate and roto-evaporated to dryness yielding oil, which was used directly in the next step of synthesis. (m=0.87 g. Yield: 98%)

(C) N-(3-(2-ethoxy-6-methoxy-1H-benzimidazol-1-yl)propyl) acetamide

In a 50 ml reactor containing N-(3-((2-amino-5-methoxyphenyl)amino)propyl)acetamide (500 mg, 2.10 mmol), tetraethyl orthocarbonate (1.62 g, 8.4 mmol) and subsequently acetic acid (0.013 g, 0.210 mmol) were added. The reaction was heated to 80° C. and kept at this temperature for 30 min. Then the reaction medium was allowed to return to room temperature and ethyl ether (25 ml) was added. The precipitated solid was filtered and washed with ethyl ether (25 ml). The product was purified by MPLC (CHCl3:MeOH 9:1) resulting in a white solid product. (m=356 mg. Yield: 58%)

$^1$H NMR (300 MHz, CHLOROFORM-d) δ ppm 1.49 (t, J=7.12 Hz, 3H) 1.93-2.09 (m, 5H) 3.25 (q, J=6.68 Hz, 2H) 3.75-4.08 (m, 6H) 4.59 (q, J=7.09 Hz, 2H) 5.59 (br s, 1H) 6.68 (d, J=2.26 Hz, 1H) 6.78 (dd, J=8.64, 2.44 Hz, 1H) 7.42 (d, J=8.64 Hz, 1H);

$^{13}$C NMR (75 MHz, CHLOROFORM-d) δ ppm 14.78 (s, 1C) 23.28 (s, 1C) 28.56 (s, 1C) 36.86 (s, 1C) 39.50 (s, 1C) 56.05 (s, 1C) 66.21 (s, 1C) 93.90 (s, 1C) 108.71 (s, 1C) 118.11 (s, 1C) 133.86 (s, 1C) 134.22 (s, 1C) 155.37 (s, 1C) 156.74 (s, 1C) 170.15 (s, 1C).

Example 9

N-(3-(2,6-dimethoxy-1H-benzimidazol-1-yl) propyl) acetamide

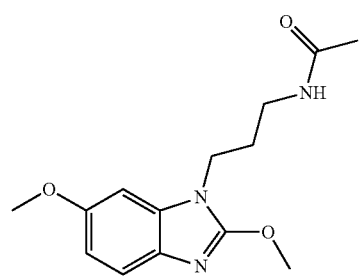

(140)

In a 50 ml reactor containing N-(3-((2-amino-5-methoxyphenyl)amino)propyl) acetamide (Example 8 (B)) (400 mg, 1.69 mmol), tetramethylorthocarbonate (92 g, 6.74 mmol) and subsequently acetic acid (0.010 g, 0.169 mmol) were added. The reaction was heated to 80° C. and kept at this temperature for 30 min. Then the reaction medium was allowed to return to room temperature and ethyl ether (25 ml) was added. The precipitated solid was filtered, washed with ethyl ether (25 ml) and purified by MPLC (CHCl3: MeOH 9:1) resulting in a white solid product. (m=271 mg. Yield: 58%)

$^1$H NMR (300 MHz, CHLOROFORM-d) δ ppm 1.92-2.08 (m, 5H) 3.26 (q, J=6.72 Hz, 2H) 3.75-3.86 (m, 3H) 3.93-4.20 (m, 6H) 5.57 (br s, 1H) 6.68 (d, J=2.32 Hz, 1H) 6.78 (dd, J=8.68, 2.44 Hz, 1H) 7.43 (d, J=8.62 Hz, 1H);

$^{13}$C NMR (75 MHz, CHLOROFORM-d) δ ppm 23.26 (s, 1C) 28.67 (s, 1C) 37.00 (s, 1C) 39.68 (s, 1C) 56.03 (s, 1C) 57.17 (s, 1C) 93.91 (s, 1C) 108.75 (s, 1C) 118.19 (s, 1C) 134.06 (s, 1C) 155.42 (s, 1C) 157.32 (s, 1C) 170.21 (s, 1C).

Example 10

N-(2-(2,6-dimethoxy-1H-benzimidazol-1-yl)ethyl) acetamide

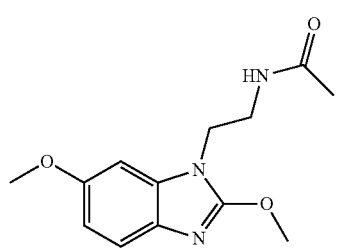

(118)

In a 50 ml reactor containing N-(2-((2-amino-5-methoxyphenyl) amino)ethyl)acetamide (Example 1 (B)) (550 mg, 2.46 mmol), tetramethylorthocarbonate, (1.34 g, 9.85 mmol) and subsequently acetic acid (0.015 g, 0.250 mmol) were added. The reaction was heated to 80° C. and kept at this temperature for 30 min. Then the reaction medium was allowed to return to room temperature and ethyl ether (25 ml) was added. The precipitated solid was filtered, washed with ethyl ether (25 ml) and purified by MPLC (CHCl3:MeOH 9:1) resulting in a white solid product. (m=344 mg. Yield: 53%)

¹H NMR (300 MHz, CHLOROFORM-d) δ ppm 1.92 (s, 3H) 3.57 (q, J=5.92 Hz, 2H) 3.83 (s, 3H) 4.06-4.13 (m, 5H) 5.83 (br s, 1H) 6.72 (d, J=2.68 Hz, 1H) 6.75-6.81 (m, 1H) 7.40 (d, J=8.62 Hz, 1H);

¹³C NMR (75 MHz, CHLOROFORM-d) δ ppm 23.13 (s, 1C) 38.96 (s, 1C) 41.24 (s, 1C) 55.99 (s, 1C) 57.02 (s, 1C) 93.45 (s, 1C) 109.32 (s, 1C) 118.16 (s, 1C) 133.82 (s, 1C) 134.56 (s, 1C) 155.61 (s, 1C) 157.34 (s, 1C) 170.69 (s, 1C)

Example 11

N-(2-(2,6-dimethoxy-1H-benzimidazol-1-yl)ethyl)propionamide

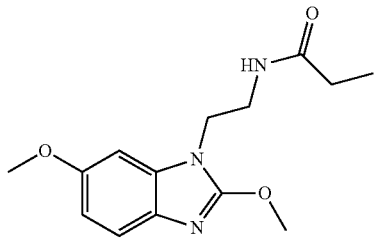

(138)

In a 50 ml reactor containing N-(2-((2-amino-5-methoxyphenyl)amino)ethyl)propionamide (Example 2 (B)) (200 mg, 0.84 mmol), tetramethylorthocarbonate(0.460 g, 3.37 mmol) and subsequently acetic acid (0.010 g, 0.167 mmol) were added. The reaction was heated to 80° C. and kept at this temperature for 30 min. Then the reaction medium was allowed to return to room temperature and ethyl ether (10 ml) was added. The precipitated solid was filtered, washed with ethyl ether (10 ml) and purified by MPLC (CHCl3:MeOH 9:1) resulting in a white solid product. (m=129 mg. Yield: 55%)

¹H NMR (500 MHz, CHLOROFORM-d) δ ppm 1.10 (t, J=7.63 Hz, 3H) 2.13 (q, J=7.63 Hz, 2H) 3.58 (q, J=5.85 Hz, 2H) 3.68-3.88 (m, 3H) 3.97-4.17 (m, 5H) 5.66 (br s, 1H) 6.71 (d, J=2.44 Hz, 1H) 6.78 (dd, J=8.54, 2.44 Hz, 1H) 7.42 (d, J=8.70 Hz, 1H)

Example 12

N-(2,6-dimethoxy-1H-benzimidazol-1-yl)ethyl)butyramide

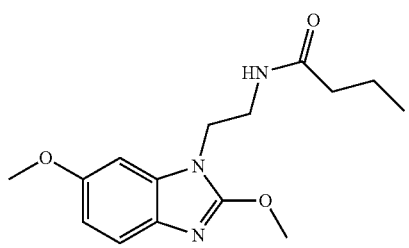

(139)

In a 10 ml reactor containing N-(2-((2-amino-5-methoxyphenyl)amino)ethyl)butyramide (Example 3 (B)) (100 mg, 0.398 mmol), tetramethylorthocarbonate(0.217 g, 1.59 mmol) and subsequently acetic acid (0.024 g, 0.0398 mmol) were added. The reaction was heated to 80° C. and kept at this temperature for 30 min. Then the reaction medium was allowed to return to room temperature and ethyl ether (5 ml) was added. The precipitated solid was filtered, washed with ethyl ether (5 ml) and purified by MPLC (CHCl3:MeOH 9:1) resulting in a white solid product. (m=55.6 mg. Yield: 48%)

¹H NMR (500 MHz, CHLOROFORM-d) δ ppm 0.91 (t, J=7.40 Hz, 3H) 1.68-1.75 (m, 2H) 2.08 (t, J=7.55 Hz, 2H) 3.44-3.64 (m, 2H) 3.71-3.88 (m, 3H) 4.04-4.17 (m, 6H) 5.65 (br s, 1H) 6.72 (d, J=2.44 Hz, 1H) 6.78 (dd, J=8.70, 2.44 Hz, 1H) 7.42 (d, J=8.70 Hz, 1H)

Example 13

N-(1-(2-Ethoxy-6-methoxy-1H-benzimidazol-1-yl)propan-2-yl)acetamide

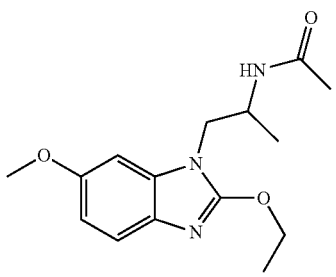

(136)

(A) N¹-(5-methoxy-2-nitrophenyl)propane-1,2-diamine

In a 10 ml reactor with magnetic stirring, 3-chloro-4-Nitroanisole (0.5 g, 2.67 mmol), 1,2-propanediamine (3 ml, 35.2 mmol) and cupric bromide (0.250 g, 1.12 mmol) were added. The reaction medium was kept under stirring and heating at 60-65° C. for 1 hour. After cooling, the reaction medium was diluted with water and extracted three times with chloroform. The organic phases were combined and washed with water. The chloroform was dried over magnesium sulfate and roto-evaporated to dryness resulting in a yellow colored solid which was used directly in the next step. (m=0.60 g. Yield: 100%)

(B) N-(1-((5-methoxy-2-nitrophenyl)amino)propan-2-yl)acetamide

In a 50 ml reactor N1-(5-methoxy-2-nitrophenyl) propane-1,2-diamine (0.60 g, 2.67 mmol), ethanol (40 ml) and acetic anhydride (0.254 ml, 2.67 mmol) were added. The reaction medium was heated to 60° C. and kept under stirring for 1 hour. Then the ethanol was evaporated to dryness and the resulting oil dissolved in ethyl acetate and washed with 15% sodium carbonate solution. The organic phase was separated, dried with magnesium sulfate and roto-evaporated resulting in a yellow solid product, which was employed directly in the next step. (m=0.55 g. Yield: 77%)

(C) N-(1-((2-amino-5-methoxyphenyl)amino)propan-2-yl) acetamide

In a 100 ml reactor, N-(1-((5-methoxy-2-nitrophenyl)amino)propan-2-yl)acetamide (0.55 g, 2.06 mmol) and methanol (35 ml) were added. The system was kept under stirring with heating between 40 and 50° C. until complete dissolution of the solid. Then the reaction medium was cooled to room temperature and powdered zinc (2.0 g, 30.6 mmol) and ammonium formate (0.97 g, 15.4 mmol) were added under vigorous stirring. The resulting mixture was kept under stirring for approximately 30 minutes and then gravity filtered. The filtrate was roto-evaporated and the resulting residue was extracted with dichloromethane (300 ml). The dichloromethane was washed with 6N sodium hydroxide solution (2×200 ml) and sodium chloride solution (300 ml). The organic phase was separated, dried with magnesium sulfate and roto-evaporated yielding the product as oil, which was used directly in the next step. (m=0.41 g Yield: 84%)

(D) N-(1-(2-Ethoxy-6-methoxy-1H-benzimidazol-1-yl)propan-2-yl) acetamide

In a 50 ml reactor containing N-(1-((2-amino-5-methoxyphenyl)amino)propan-2-yl)acetamide (400 mg, 1.69 mmol), tetraethyl orthocarbonate (1.3 g, 6.7 mmol) and subsequently acetic acid (0.010 g, 0.169 mmol) were added. The reaction was heated to 80° C. and kept at this temperature for 30 min. Then the reaction medium was allowed to return to room temperature and ethyl ether (25 ml) was added. The precipitated solid was filtered, washed with ethyl ether (25 ml) and purified by MPLC (CHCl3:MeOH 9:1) resulting in a white solid product. (m=240 mg. Yield: 49%)

$^1$H NMR (500 MHz, CHLOROFORM-d) δ ppm 1.18 (d, J=6.87 Hz, 3H) 1.44-1.54 (m, 5H) 1.94 (s, 3H) 3.83-3.90 (m, 4H) 3.97-4.07 (m, 2H) 4.31-4.39 (m, 1H) 4.47-4.69 (m, 3H) 5.51 (br d, J=7.17 Hz, 1H) 6.74-6.79 (m, 1H) 6.88 (d, J=2.44 Hz, 1H) 7.40 (d, J=8.55 Hz, 1H)

Example 14

2-Bromo-N-(2-(2-ethoxy-6-methoxy-1H-benzimidazol-1-yl)ethyl) acetamide

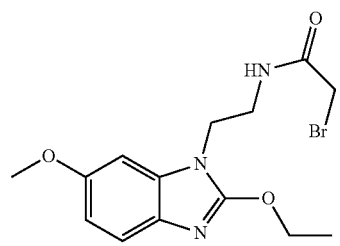

(133)

(A) 2-bromo-N-(2-((5-methoxy-2-nitrophenyl)amino)ethyl)acetamide

In a 100 ml reactor with magnetic stirring, N1-(5-methoxy-2-nitrophenyl) ethane-1,2-diamine (1 g, 4.73 mmol), dichloromethane (50 ml) and triethylamine (0.67 ml, 4.81 mmol) were added. The reaction medium was kept under stirring and a bromoacetyl bromide solution (0.413 ml, 4.74 mmol) in dichloromethane (10 ml) was slowly added through an addition funnel. The reaction medium was kept under stirring at room temperature for 2 hours. After the completion of the reaction, 10 ml of 10% aqueous hydrochloric acid solution (10 ml) was added. The dichloromethane was separated and the aqueous phase extracted with dichloromethane (2×20 ml). The organic phase was washed with 5% aqueous bicarbonate solution (100 ml) and saturated sodium chloride solution (100 ml). The organic extract was separated, dried with anhydrous magnesium sulfate and roto-evaporated, resulting in a yellow solid product which was used directly in the next step. (m=1.45 g. Yield: 92%)

(B) N-(2-((2-amino-5-methoxyphenyl)amino)ethyl)-2-bromoacetamide

In a 100 ml reactor, 2-bromo-N-(2-((5-methoxy-2-nitrophenyl)amino)ethyl)acetamide (0.70 g, 2.31 mmol) and methanol (50 ml) were added. The system was kept under stirring with heating between 40 and 50° C. until complete dissolution of the solid. Then the reaction medium was cooled to room temperature and powdered zinc (2.05, 31.4 mmol) and ammonium formate (1.0 g, 15.9 mmol) were added under vigorous stirring. The resulting mixture was kept under stirring for approximately 30 minutes and then gravity filtered. The filtrate was roto-evaporated and the resulting residue was extracted with 350 ml of dichloromethane. The dichloromethane was washed with 6N sodium hydroxide solution (2×200 ml) and sodium chloride solution(300 ml). The organic phase was separated, dried with magnesium sulfate and roto-evaporated resulting in a product as oil, which was used directly in the next step. (m=0.57 g. Yield: 90%)

(C) 2-Bromo-N-(2-(2-ethoxy-6-methoxy-1H-benzimidazol-1-yl)ethyl)acetamide

In a 50 ml reactor containing N-(2-((2-amino-5-methoxyphenyl)amino)ethyl)-2-bromoacetamide (570 mg, 1.89 mmol), tetraethyl orthocarbonate (1.45 g, 7.5 mmol) and subsequently acetic acid (0.113 g, 0.189 mmol) were added. The reaction was heated to 80° C. and kept at this temperature for 30 min. Then the reaction medium was allowed to return to room temperature and ethyl ether (25 ml) was added. The precipitated solid was filtered, washed with ethyl ether (25 ml) and purified by MPLC (CHCl3:MeOH 9:1) resulting in a white solid product. (m=362 mg. Yield: 54%)

$^1$H NMR (500 MHz, CHLOROFORM-d) δ ppm 1.40-1.50 (m, 3H) 3.58-3.70 (m, 2H) 3.71-3.87 (m, 6H) 3.94-4.16 (m, 2H) 4.55-4.62 (m, 2H) 6.62-6.70 (m, 1H) 6.72 (d, J=2.44 Hz, 1H) 6.78 (d, J=8.27 Hz, 1H) 7.42 (d, J=8.70 Hz, 1H)

Example 15

N-(2-(6-methoxy-2-(methylthio)-1H-benzimidazol-1-yl)ethyl)acetamide

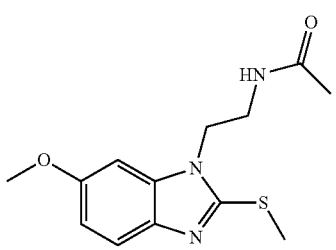

(123)

(A) N-(2-(2-mercapto-6-methoxy-1H-benzimidazol-1-yl)ethyl) acetamide

In a 10 ml reactor N-(2-((2-amino-5-methoxyphenyl)amino)ethyl) acetamide (1.340 g, 6.00 mmol) and thiourea (0.457 g, 6.00 mmol) were added. The mixture was initially heated to 120° C. for 10 min with intense vapor release and then heated to 160° C. for 5 min, with second vapor release. The temperature was reduced to 80° C. and ethanol (15 ml) was added. The resulting mixture was cooled to −10° C., the solid filtered and washed with ice cold ethanol (10 ml), yielding 1.26 g (79%) of the crude product, which was purified by MPLC (CHCl3/MeOH 9:1) resulting the title compound as a rosy solid. (m=1.1 g. Yield: 69.1%)

(B) N-(2-(6-methoxy-2-(methylthio)-1H-benzimidazol-1-yl)ethyl) acetamide

Potassium carbonate (13.02 mg, 0.094 mmol) followed by iodomethane (5.89 μl, 0.094 mmol) were added to a solution of N-(2-(2-mercapto-6-methoxy-1H-benzimidazol-1-Yl)ethyl)acetamide (50.0 mg, 0.188 mmol) in acetone (2 ml) at 0° C. The reaction was kept under stirring at room temperature for 1 h. After, a second portion of potassium carbonate (13.02 mg, 0.094 mmol) and iodometane (5.89 μl, 0.094 mmol) were added and the mixture remained under stirring overnight at room temperature. Volatile portion was removed under reduced pressure and the residue partitioned between ethyl acetate (10 ml) and water (10 ml). The organic extract was separated, dried with magnesium sulfate and evaporated under reduced pressure to yield the pure product. (m=44 mg. Yield: 84%)

$^1$H NMR (500 MHz, CHLOROFORM-d) δ ppm 1.93 (s, 3H) 2.76 (s, 3H) 3.61 (q, J=5.95 Hz, 2H) 3.82-3.86 (m, 3H) 4.24 (t, J=5.80 Hz, 2H) 6.79 (s, 1H) 6.84 (d, J=8.76 Hz, 1H) 7.27 (s, 1H) 7.54 (d, J=8.70 Hz, 1H)

Example 16

N-(2-(2-ethoxy-7,8-dihydro-1H-benzofuran[4,5-d]imidazol-1-yl)ethyl) acetamide

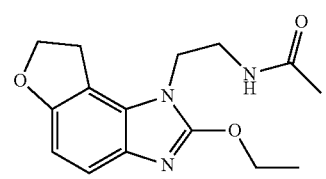

(148)

(A) tert-Butyl(2-(2-ethoxy-7,8-dihydro-1H-benzofuran[4,5-d]imidazol-1-yl)ethyl)carbamate In a 25 ml reactor containing tert-butyl(2-((5-amino-2,3-dihydrobenzofuran-4-yl)amino)ethyl)carbamate (200 mg, 0.682 mmol), tetraethyl orthocarbonate (524 mg, 2.727 mmol) followed by acetic acid (4 mg, 0.038 mmol) were added. The reaction was heated to 80° C. and kept at this temperature for 30 min. Then the reaction medium was allowed to return to room temperature and ethyl ether (10 ml) was added. The precipitated solid was filtered, washed with ethyl ether (10 ml) and purified by MPLC (CHCl3:MeOH 9:1) resulting in a white solid product. (m=181 mg. Yield: 76%)

(B) 2-(2-ethoxy-7,8-dihydro-1H-benzofuran[4,5-d]imidazol-1-yl)ethanamine

In a 25 ml reactor, tert-Butyl(2-(2-ethoxy-7,8-dihydro-1H-benzofuran[4,5-d]imidazol-1-yl)ethyl)carbamate (150 mg, 0.432 mmol) were dissolved in 6 ml dichloromethane. Next trifluoroacetic acid (0.266 ml, 3.451 mmol) was added. The reaction was stirred at room temperature for 6 h (monitored by HPLC). After the reaction was complete, the reaction medium was transferred to a beaker and diluted with dichloromethane (50 ml). A 15% aqueous sodium carbonate solution was added under vigorous stirring until pH=12. The organic phase was separated, dried with magnesium sulfate and evaporated resulting in a white solid product, which was used directly in the next step. (m=80 mg. Yield: 75%)

(C) N-(2-(2-ethoxy-7,8-dihydro-1H-benzofuran[4,5-d]imidazol-1-yl)ethyl)acetamide In a 25 ml reactor, ethanol (10 mg), 2-(2-ethoxy-7,8-dihydro-1H-benzofuran[4,5-d]imidazol-1-yl)ethanamine (70 mg, 0.283 mmol), acetic anhydride (0.030 ml, 0.311 mmol) and sodium carbonate (33 mg, 0.311 mmol) were added. The reaction mixture was heated under reflux for 1 h and then evaporated under reduced pressure. The resulting oil was dissolved in ethyl acetate (30 ml) and washed with 10% aqueous sodium carbonate solution (10 ml). The organic extract was dried over magnesium sulfate, rotoevaporated and the resulting solid purified by chromatography (MPLC) (CHCl3:MeOH 9:1) resulting in a white solid product. (m=75 mg. Yield: 92%)

$^1$H NMR (300 MHz, CHLOROFORM-d) δ ppm 1.44 (t, J=7.09 Hz, 3H) 1.86-1.97 (m, 3H) 3.38-3.65 (m, 5H) 4.11 (t, J=6.11 Hz, 2H) 4.45-4.72 (m, 4H) 5.92 (br s, 1H) 6.68 (d, J=8.46 Hz, 1H);

$^{13}$C NMR (75 MHz, CHLOROFORM-d) δ ppm 14.76 (s, 1C) 23.12 (s, 1C) 28.09 (s, 1C) 39.82 (s, 1C) 41.98 (s, 1C) 66.15 (s, 1C) 71.43 (s, 1C) 103.82 (s, 1C) 106.28 (s, 1C) 116.53 (s, 1C) 130.54 (s, 1C) 134.43 (s, 1C) 156.53 (s, 1C) 156.68 (S, 1C) 170.59 (s, 1C).

Example 17

N-(2-(2-methoxy-7,8-dihydro-1H-benzofuran[4,5-d]imidazol-1-yl)ethyl) acetamide

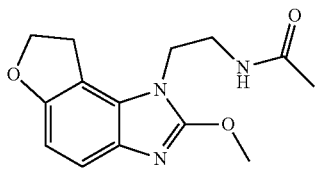

(150)

(A) tert-Butyl(2-(2-methoxy-7,8-dihydro-1H-benzofuran[4,5-d]imidazol-1-yl)ethyl)carbamate In a 10 ml reactor containing tert-butyl (2-((5-amino-2,3-dihydrobenzofuran-4-yl)amino)ethyl)carbamate (200 mg, 0.682 mmol), tetramethylorthocarbonate (374 mg, 2.728 mmol) and subsequently acetic acid (4 mg, 0.038 mmol) were added. The reaction was heated to 80° C. and kept at this temperature for 30 min. Then the reaction medium was allowed to return to room temperature and ethyl ether (10 ml) was added. The precipitated solid was filtered, washed with ethyl ether (10 ml) and purified by MPLC (CHCl3:MeOH 9:1) resulting in white solid a product. (m=160 mg. Yield: 70%)

(B) 2-(2-methoxy-7,8-dihydro-1H-benzofuran[4,5-d]imidazol-1-yl)ethanamine

In a 25 ml reactor, tert-Butyl(2-(2-methoxy-7,8-dihydro-1H-benzofuran[4,5-d]imidazol-1-yl)ethyl)carbamate (113 mg, 0.399 Mmol) was added to 5 ml dichloromethane. Then trifluoroacetic acid (0.209 ml, 2.71 mmol) was added. The reaction was stirred at room temperature for 6 h (monitored by HPLC). After the reaction was complete, the reaction medium was transferred to a beaker and diluted with dichloromethane (50 ml). A 15% aqueous sodium carbonate solution was added Under vigorous stirring until pH=12. The organic phase was separated, dried with magnesium sulfate and evaporated resulting in a white solid product, which was used directly in the next step. (m=55 mg. Yield: 69.6%)

(C) N-(2-(2-methoxy-7,8-dihydro-1H-benzofuran[4,5-d]imidazol-1-yl)ethyl)acetamide In a 25 ml reactor, ethanol (10 ml), 2-(2-methoxy-7,8-dihydro-1H-benzofuran[4,5-d]imidazol-1-yl) ethanamine (55 mg, 0.236 mmol), acetic anhydride (0.025 ml, 0.259 mmol) and sodium carbonate (27.5 mg, 0.258 mmol) were added. The reaction mixture was heated under reflux for 1 h and then evaporated under reduced pressure. The obtained oil was dissolved in ethyl acetate (30 ml) and washed with 10% aqueous sodium carbonate solution (10 ml). The organic extract was dried over magnesium sulfate, roto-evaporated and the resulting solid was purified by chromatography (MPLC) (CHCl3:MeOH 9:1) resulting in a white solid product. (m=58 mg. Yield: 89%)

$^1$H NMR (300 MHz, CHLOROFORM-d) δ ppm 1.95 (s, 3H) 3.38-3.61 (m, 5H) 4.06-4.13 (m, 6H) 4.63 (t, J=8.59 Hz, 2H) 5.95 (br s, 1H) 6.68 (d, J=8.44 Hz, 1H);
$^{13}$C NMR (75 MHz, CHLOROFORM-d) δ ppm 23.10 (s, 1C) 28.05 (s, 1C) 39.74 (s, 1C) 42.02 (s, 1C) 57.02 (s, 1C) 71.45 (s, 1C) 103.87 (s, 1C) 106.33 (s, 1C) 116.64 (s, 1C) 130.76 (s, 1C) 134.30 (s, 1C) 156.77 (s, 1C) 157.13 (s, 1C) 170.67 (S, 1C).

Example 18

N-(2-(5-bromo-2-ethoxy-6-methoxy-1H-benzimidazole-1-yl)ethyl) acetamide

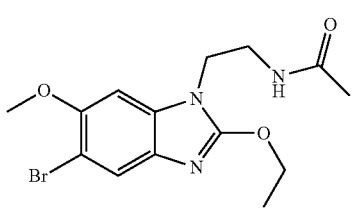

(117)

In a 10 ml reactor, N-(2-(2-ethoxy-6-methoxy-1H-benzimidazole-1-yl)ethyl)acetamide (Example 1) (100 mg, 0.360 mmol), chloroform (5 ml) and N-bromosuccinimide (64 mg, 360 mmol) were added. The reaction medium was under reflux and kept under stirring for 8 hours. The reaction medium was diluted with chloroform (50 ml), the organic phase was washed with 5% aqueous sodium carbonate solution (3×30 ml), dried with magnesium sulfate, roto-evaporated and purified by chromatography resulting in a white solid product. (m=70 mg. Yield: 54%)

$^1$H NMR (500 MHz, CHLOROFORM-d) δ ppm 1.46 (t, J=7.10 Hz, 3H) 1.89-1.93 (m, 3H) 3.56 (q, J=5.95 Hz, 2H) 3.88-3.92 (m, 3H) 4.13 (t, J=5.87 Hz, 2H) 4.51-4.59 (m, 2H) 5.71 (br s, 1H) 6.79 (s, 1H) 7.67 (s, 1H)

Example 19

N-(2-(5-chloro-2-ethoxy-6-methoxy-1H-benzimidazole-1-yl)ethyl) acetamide

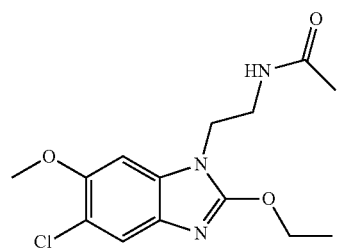

(121)

In a 50 ml reactor N-(2-(2-ethoxy-6-methoxy-1H-benzimidazole-1-yl)ethyl)acetamide (Example 1) (0.5 g, 1.80 mmol), isopropanol (25 ml) and N-chlorosuccinimide (0.241 g, 1.80 mmol) were added. The reaction medium was under reflux and kept under heating and stirring for 24 hours. After the reaction was complete, the reaction medium was roto-evaporated to dryness and diluted with chloroform (200 ml). The chloroform was washed with 5% aqueous sodium carbonate solution (3×150 ml), dried with anhydrous magnesium sulfate and roto-evaporated. The residue containing the raw product was purified by chromatography resulting in a white solid product. (m=345 mg. Yield: 61%)

$^1$H NMR (500 MHz, CHLOROFORM-d) δ ppm 1.44-1.50 (m, 3H) 1.89-1.93 (m, 3H) 3.47-3.72 (m, 2H) 3.89-3.93 (m, 3H) 4.12 (t, J=5.87 Hz, 2H) 4.44-4.68 (m, 2H) 7.27 (s, 1H) 7.50 (s, 1H);
$^{13}$C NMR (75 MHz, CHLOROFORM-d) δ ppm 14.70 (s, 1C) 23.17 (s, 1C) 39.02 (s, 1C) 41.13 (s, 1C) 56.95 (s, 1C) 66.41 (s, 1C) 93.00 (s, 1C) 116.67 (s, 1C) 118.99 (s, 1C) 133.00 (s, 1C) 133.82 (s, 1C) 150.76 (s, 1C) 157.05 (s, 1C) 170.76 (s, 1C).

Example 20

N-(3-(5-chloro-2-ethoxy-6-methoxy-1H-benzimidazole-1-yl)propyl)acetamide

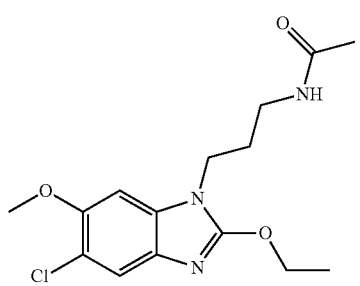

(142)

In a 10 ml reactor, N-(3-(2-ethoxy-6-methoxy-1H-benzimidazole-1-yl)propyl)acetamide (Example 8) (50 mg, 0.172 mmol), N-chlorosuccinimide (23 mg, 0.172 mmol) and isopropanol (2 ml) were added. The reaction medium was kept under reflux and stirred for 18 hours, then poured into chloroform (40 ml). The organic phase was washed with 5% aqueous sodium carbonate solution (3×20 ml), dried with magnesium sulfate, roto-evaporated and the residue purified by flash chromatography resulting in a white solid. (m=42 mg. Yield: 75%).

$^1$H NMR (300 MHz, CHLOROFORM-d) δ ppm 1.49 (t, J=7.09 Hz, 3H) 1.94-2.03 (m, 5H) 3.26 (q, J=6.68 Hz, 2H) 3.92-4.03 (m, 5H) 4.59 (q, J=7.12 Hz, 2H) 5.58 (br s, 1H) 6.72 (s, 1H) 7.53 (s, 1H);

$^{13}$C NMR (75 MHz, CHLOROFORM-d) δ ppm 14.74 (s, 1C) 23.30 (s, 1C) 28.73 (s, 1C) 36.91 (s, 1C) 39.70 (s, 1C) 57.10 (s, 1C) 66.47 (s, 1C) 93.23 (s, 1C) 116.80 (s, 1C) 119.13 (s, 1C) 132.36 (s, 1C) 134.12 (s, 1C) 150.68 (s, 1C) 157.06 (s, 1C) 170.18 (s, 1C).

Example 21

N-(3-(5-chloro-2,6-dimethoxy-1H-benzimidazole-1-yl) propyl)acetamide

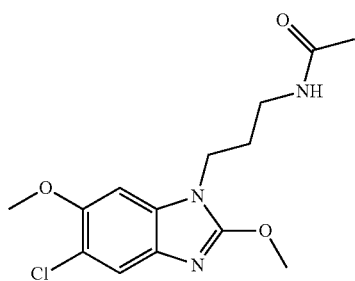

(144)

In a 10 ml reactor, N-(3-(2,6-dimethoxy-1H-benzimidazole-1-yl)propyl)acetamide (Example 9) (48.5 mg, 0.175 mmol), N-chlorosuccinimide (24.1 mg, 0.180 mmol) and isopropanol (2 ml) were added. The reaction medium was kept under reflux and stirred for 6 hours, then poured into chloroform (40 ml). The organic phase was washed with 5% aqueous sodium carbonate solution (3×20 ml), dried with magnesium sulfate, roto-evaporated and the residue purified by chromatography resulting in a white solid. (m=37 mg. Yield: 68%).

$^1$H NMR (500 MHz, CHLOROFORM-d) δ ppm 1.82-2.13 (m, 5H) 3.27 (q, J=6.82 Hz, 2H) 3.84-3.94 (m, 3H) 3.99 (t, J=6.87 Hz, 2H) 4.11-4.19 (m, 3H) 5.54 (br s, 1H) 6.72 (s, 1H) 7.54 (s, 1H)

Example 22

N-(2-(5-chloro-2,6-dimethoxy-1H-benzimidazole-1-yl)ethyl) acetamide

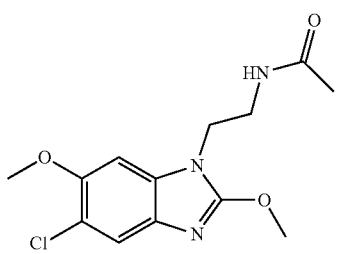

(143)

In a 10 ml reactor, N-(2-(2,6-dimethoxy-1H-benzimidazole-1-yl)ethyl)acetamide (Example 10) (60 mg, 0.228 mmol), N-chlorosuccinimide(30.4 mg, 0.228 mmol) and isopropanol (3 ml) were added. The reaction medium was kept under reflux and stirred for 96 hours, then poured into chloroform (40 ml). The organic phase was washed with 5% aqueous sodium carbonate solution (3×20 ml), dried with magnesium sulfate, roto-evaporated and the residue purified by flash chromatography resulting in a white solid. (m=18 mg. Yield: 27%)

$^1$H NMR (300 MHz, CHLOROFORM-d) δ ppm 1.88-1.96 (m, 3H) 3.52-3.68 (m, 2H) 3.92 (s, 3H) 4.09-4.17 (m, 5H) 6.80 (s, 1H) 7.52 (s, 1H);

$^{13}$C NMR (75 MHz, CHLOROFORM-d) δ ppm 23.16 (s, 1C) 39.02 (s, 1C) 41.14 (s, 1C) 56.94 (s, 1C) 57.25 (s, 1C) 93.02 (s, 1C) 116.74 (s, 1C) 119.10 (s, 1C) 133.18 (s, 1C) 133.66 (s, 1C) 150.85 (s, 1C) 157.61 (s, 1C) 170.83 (s, 1C).

Example 23

N-(2-(5-chloro-2-ethoxy-6-methoxy-1H-benzimidazole-1-yl)ethyl)cyclopropanecarboxamide

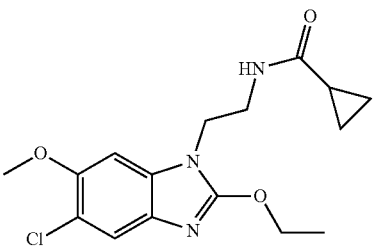

(141)

In a 10 ml reactor, N-(2-(2-ethoxy-6-methoxy-1H-benzimidazole-1-yl)ethyl)cyclopropane carboxamide (Example 4) (92 mg, 0.329 mmol), N-Chlorosuccinimide (45 mg, 0.337 mmol) and isopropanol (4 ml) were added. The reaction medium was kept under reflux and stirred for 24 hours, then poured into chloroform (60 ml). The organic phase was washed with 5% aqueous sodium carbonate solution (3×30 ml), dried with magnesium sulfate, roto-evaporated and the residue purified by chromatography resulting in a white solid. (m=61 mg. Yield: 60%).

$^1$H NMR (500 MHz, CHLOROFORM-d) δ ppm 0.66-0.85 (m, 2H) 0.87-1.02 (m, 2H) 1.20-1.34 (m, 1H) 1.46 (t, J=7.10 Hz, 3H) 3.57-3.74 (m, 2H) 3.89-3.98 (m, 3H) 4.11 (t, J=5.80 Hz, 2H) 4.45-4.66 (m, 2H) 6.76 (s, 1H) 7.27 (s, 1H) 7.50 (s, 1H).

Example 24

N-(2-(7-chloro-2-ethoxy-6-methoxy-1H-benzimidazole-1-yl)ethyl) acetamide

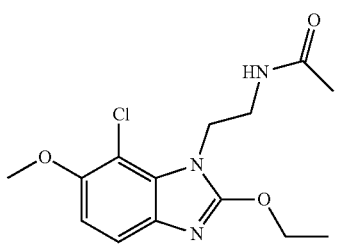

(151)

In a 125 ml reactor, N-(2-(2-ethoxy-6-methoxy-1H-benzimidazole-1-yl)ethyl)acetamide (Example 1) (0.5 g, 1.80 mmol), chloroform (50 ml) and N-chlorosuccinimide (0.270 g, 2.02 mmol) were added. The reaction medium was under reflux and kept under heating and stirring for 48 hours. After this period, the reaction medium was roto-evaporated to dryness and diluted with chloroform (200 ml). The chloroform was washed with 5% aqueous sodium carbonate solution (3×150 ml), dried with anhydrous magnesium sulfate and roto-evaporated. The residue was fractionated by chromatography resulting in a white solid product. (m=128 mg. Yield: 23%).

$^1$H NMR (300 MHz, DMSO-d$_6$) δ ppm 1.38 (t, J=6.97 Hz, 3H) 1.74 (s, 3H) 3.33-3.40 (m, 3H) 3.84 (s, 3H) 4.28 (t, J=5.87 Hz, 2H) 4.47 (q, J=7.09 Hz, 2H) 6.93 (d, J=8.44 Hz, 1H) 7.31 (d, J=8.80 Hz, 1H) 7.99 (br t, J=5.87 Hz, 1H);

$^{13}$C NMR (75 MHz, DMSO-d$_6$) δ ppm 14.41 (s, 1C) 22.45 (s, 1C) 42.15 (s, 1C) 56.94 (s, 1C) 66.07 (s, 1C) 102.83 (s, 1C) 106.80 (s, 1C) 115.80 (s, 1C) 130.18 (s, 1C) 135.87 (s, 1C) 149.98 (s, 1C) 157.30 (s, 1C) 169.44 (s, 1C).

2. Tests Conducted and Test Results

The examples described herein are for the sole purpose of exemplifying one of a number of ways of carrying out the invention, but are not limited to the scope thereof.

DESCRIPTION OF TABLES

Table 1: Binding and functional assays results on melatonergic receptors MT1 and MT2 for selected compounds.
Table 2: Permeability study results onCaco-2 cells (10-6 cm/s).
Table 3: Water solubility study results, expressed as μM.
Table 4: Intrinsic clearance study results on cryopreserved human hepatocytes, expressed as half-life (minutes).
Table 5: Results for the inhibition study in human recombinant cytochromes (CYP), expressed as percent inhibition (%)
Table 6: Pharmacokinetic profile study results in CD-1 mice and Wistar-Han mice after oral (10 mg/kg) and intravenous (1 mg/kg) administration of the compounds.
2.1—MT1 and MT2—Binding The binding assay was performed in melatonergic MT1 and MT2 receptors in order to check the receptor affinity for the ligand, i.e., the ability of the molecule to bind to the respective receptors. The Ki described in the results is the dissociation constant and measures the affinity of a non-radioactive test compound for the receptor. The IC50 shows the concentration of the substance required for achieving 50% inhibition of the receptors. Kd shows the affinity of the radio ligand to the receptor. Receptor inhibition is measured by the % of inhibition a binding specific control. Recombinant human cells (CHO-derived) and [1251]2-iodomelatonin compound labeling were used followed by incubation and detection at concentration of 0.01-0.05 nM by Scintillation Count, with Kd 0.04 nM and 0.085 nM, respectively. Incubation was performed for 60-120 min at 37° C.

According to the results, agomelatine showed high affinity to the melatonergic receptor MT1 (Ki 0.2 nM) and MT2 (Ki 0.042 nM). The inventive compounds also showed high affinity for both MT1 and MT2 receptors, as demonstrated in Table 1. The affinity of compounds 120, 121, 140, 142 and 143, expressed as affinity constant (Ki) values by the MT1 receptor was 1.1, 0.88, 2.2, 1.3 and 2.1 nM. The affinity for the MT2 receptor was 4.5, 0.93, 11, 1.6 and 0.8 nM, respectively.

TABLE 1

| Chemical structure | Compound code | MT1 Binding Ki (nM) | MT2 Binding Ki (nM) | MT1 Functional EC50 (nM) | MT2 Functional EC50 (nM) |
|---|---|---|---|---|---|
| 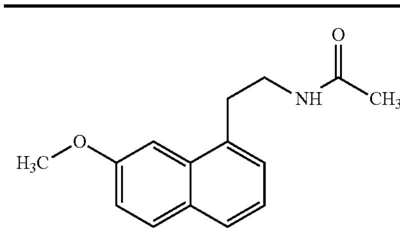 | IA2-76 (agomelatine | 0.2 | 0.042 | 0.15 | 0.019 |

TABLE 1-continued
| Chemical structure | Compound code | MT1 Binding Ki (nM) | MT2 Binding Ki (nM) | MT1 Functional EC50 (nM) | MT2 Functional EC50 (nM) |
|---|---|---|---|---|---|
| 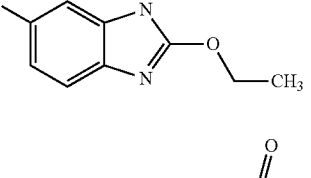 | IA2-120 | 1.1 | 4.5 | 0.19 | 0.38 |
| 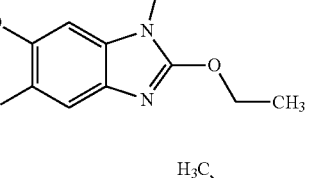 | IA2-121 | 0.88 | 0.93 | 0.16 | 0.25 |
| 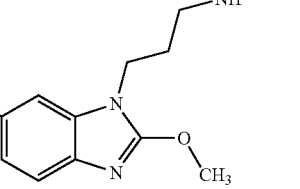 | IA2-140 | 2.2 | 11 | 2.1 | 1.2 |
| 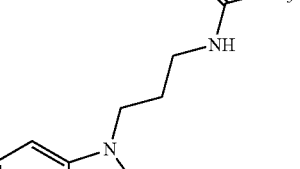 | IA2-142 | 13 | 1.6 | 3.4 | 0.39 |
| 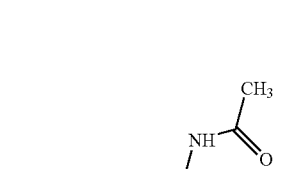 | IA2-143 | 2.1 | 0.8 | 0.25 | 2.8 |

2.2—MT1 or MT2—Functional

Functional results are assays that allow the determination of the intrinsic activity of drugs, indicating whether a compound is an agonist, antagonist or inverse agonist. The EC50 shows the drug concentration required to induce half the maximal effect, after a specific exposure time, and is usually used as way to measure the potency of a drug. As an example, we can mention the use of HEK-293 as a recombinant cell in which a specific stimulus was performed (according to the drug/compound in study), followed by incubation. The detection of the result was carried out by Cellular Dielectric Spectroscopy for impedances or by HTRF (Homogeneous Time Resolved Fluorescence) to detect IP1 (myo-Inositol 1 phosphate), a protein related to intracellular signaling.

According to the results from the assay, agomelatine behaves as an agonist and showed high potency for the MT1 receptors (EC50 0.15 nM) and MT2 (EC50 0.019 nM). The inventive compounds also behave as agonists and demonstrated high potency to the melatonergic receptors MT1 and MT2, as shown in Table 1. The potency of compounds 120, 121, 140, 142 and 143 for the MT1 receptor, expressed as EC50, was 0.19, 0.16, 2.1, 3.4, 0.25 nM. And the potency of the same compounds for the MT2 receptor was 0.38, 0.25, 1.2, 0.39 and 2.8 nM, respectively, demonstrating that compounds 120, 121 and 143 have higher potency for MT1 with respect to MT2 and compounds 140 and 142 show higher potency for MT2 with respect to MT1.

2.3—Permeability

Permeability tests were performed using Caco-2 cells, a colorectal epithelial adenocarcinoma cell line. These cells resemble intestinal epithelial cells in some aspects, such as the formation of a polarized monolayer, a well-defined brush border on the apical surface, and intercellular junctions.

The test is performed in both directions [apical to basolateral (A-B) and basolateral to apical (B-A)] through the cell monolayer, allowing an efflux ratio that provides an indicator as to whether a compound undergoes active efflux. Particle detection was performed with HPLC-MS/MS (mass spectrometry) according to the calculation of the peak area of the result. MS/MS was performed by combining two mass detectors in a single instrument.

A-B permeability was performed at pH 6.5/7.4 with incubation time of 0 and 60 minutes at 37° C. and B-A permeability was performed at pH 6.5/7.4 with incubation time of 0 and 40 minutes at 37° C.

The results in Table 2 show that the test compounds presented good permeability rate (>10-6 cm/s) in Caco-2 cells.

TABLE 2

| Chemical Structure | Molecule Code | Permeability A-B (pH 6.5/7.4) | Permeability B-A (pH 6.5/7.4) |
| --- | --- | --- | --- |
| 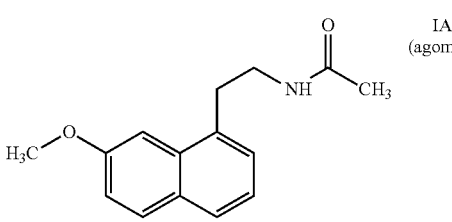 | IA2-76 (agomelatine) | 83.9 | 48.5 |
| 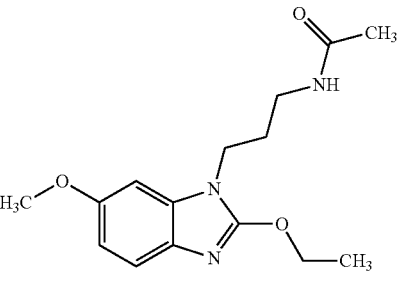 [SMILES: CCOc1nc2ccc(OC)cc2n1CCCNC(C)=O] | IA2-120 | 32.1 | 29.5 |
| 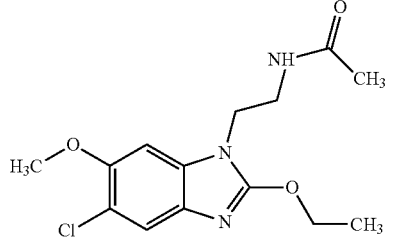 [SMILES: CCOc1nc2cc(Cl)c(OC)cc2n1CCNC(C)=O] | IA2-121 | 58.2 | 32.1 |

TABLE 2-continued

| Chemical Structure | Molecule Code | Permeability A-B (pH 6.5/7.4) | Permeability B-A (pH 6.5/7.4) |
| --- | --- | --- | --- |
| (structure) | IA2-140 | 27.3 | 55.1 |
| (structure) | IA2-142 | 34.0 | 57.8 |
| (structure) | IA2-143 | 21.3 | 71.8 |

2.4—Water Solubility

Water solubility of the present invention was determined by comparing the peak area calculation in a calibration standard (200 µM) containing organic solvent (methanol/water, 60/40, v/v) with the area calculation of the corresponding peak in a buffer sample. In addition, chromatographic purity (%) was defined as the calculation of the main peak area relative to the calculation of the peak area integrate of the standard HPLC calibration chromatogram. A standard calibration chromatogram was then generated for each compound tested along with a UV/VIS spectrum with maximal labeled absorbance. The shake-flash technique was used with constant stirring during incubation to keep a uniform medium for 24 hours in PBS at pH 7.4. The results showed that the solubility of the test compounds was similar to that of agomelatine, as shown in Table 3.

TABLE 3

| Chemical Structure | Molecule Code | PBS, pH 7.4 (µm) |
| --- | --- | --- |
| (structure) | IA2-76 (agomelatine) | 196 |

TABLE 3-continued

| Chemical Structure | Molecule Code | PBS, pH 7.4 (μm) |
|---|---|---|
| 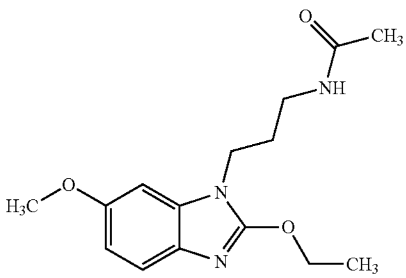 [SMILES: CCOc1nc2ccc(OC)cc2n1CCCNC(C)=O] | IA2-120 | 200 |
| 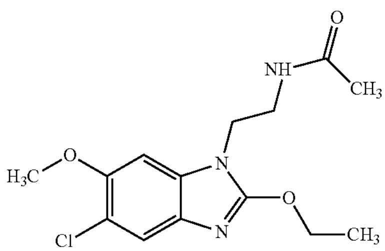 [SMILES: CCOc1nc2cc(Cl)c(OC)cc2n1CCNC(C)=O] | IA2-121 | 200 |
| 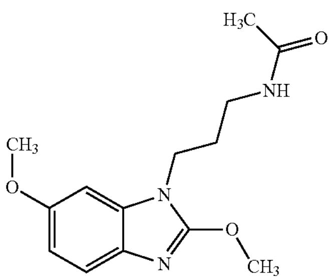 [SMILES: COc1ccc2nc(OC)n(CCCNC(C)=O)c2c1] | IA2-140 | 197.2 |
| 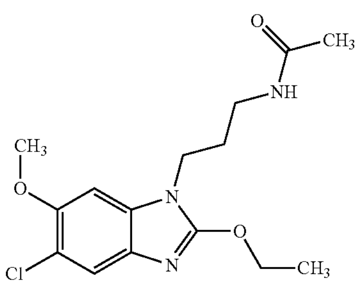 [SMILES: CCOc1nc2cc(Cl)c(OC)cc2n1CCCNC(C)=O] | IA2-142 | 180.8 |
| 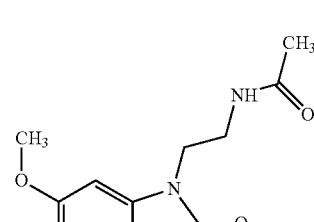 | IA2-143 | 196.7 |

2.5—Intrinsic Clearance in Human Hepatocytes

Cryopreserved hepatocytes from humans, rats (Sprague-Dawley males) and from mice (CD-1 males) were used for incubation at different times (0, 0.5, 1, 1.5, 2 hours) at 37° C. followed by HPLC-MS/MS detection. The aim was to verify the clearance time of the test substance on hepatocytes. The experiment was performed on a 96-well plate and the cryopreserved hepatocytes were thawed and resuspended in Krebs-Heinslet buffer(pH 7.3). The reaction was started by adding each test compound to each cell suspension and performing the incubation at the times indicated above. The reaction was quenched with addition of acetonitrile in the wells and detection by HPLC-MS/MS (mass spectrometry). MS/MS is performed by combining two mass detectors into a single instrument.

The half-life expressed in minutes for intrinsic clearance in human hepatocytes was greater than 120 minutes for all inventive compounds, while agomelatine had a clearance half-life of 48 minutes, as shown in FIG. 5. Similar results were seen with the compounds 120 and 121 in CD-1 mice and in Sprague-Dawley rats, compounds 120 and 121 presented clearance half-lives of 53 and 52 minutes, respectively, compared to 50 minutes for agomelatine (Table 4).

TABLE 4

| Chemical Structure | Molecule Code | Human | Rat Sprague-Dawley | Mouse CD-1 |
|---|---|---|---|---|
| 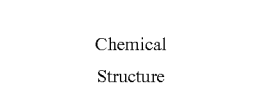 | IA2-76 (agomelatine) | 48 | 50 | 25 |

TABLE 4-continued

| Chemical Structure | Molecule Code | Human | Rat Sprague-Dawley | Mouse CD-1 |
|---|---|---|---|---|
| 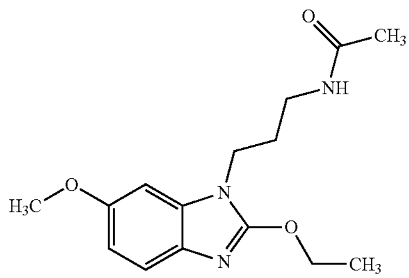 [SMILES: CCOc1nc2ccc(OC)cc2n1CCCNC(C)=O] | IA2-120 | >120 | 53 | >120 |
| 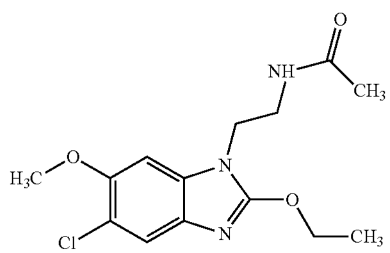 [SMILES: CCOc1nc2cc(Cl)c(OC)cc2n1CCNC(C)=O] | IA2-121 | >120 | 52 | >120 |
| 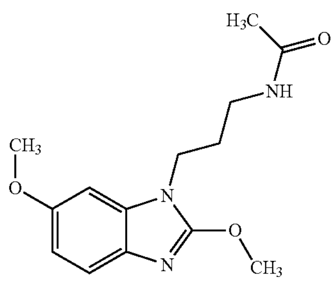 [SMILES: COc1ccc2nc(OC)n(CCCNC(C)=O)c2c1] | IA2-140 | >120 | >120.0 | >120 |
| 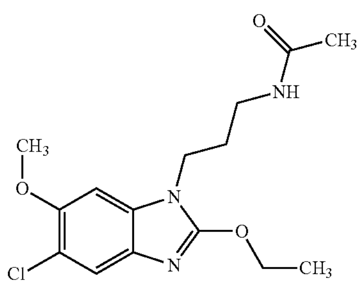 [SMILES: CCOc1nc2cc(Cl)c(OC)cc2n1CCCNC(C)=O] | IA2-142 | >120 | >120.0 | >120 |
| 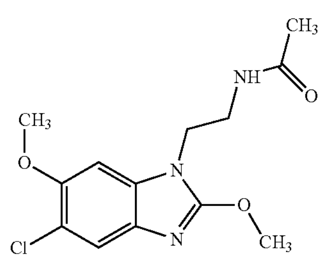 [SMILES: COc1cc2c(cc1Cl)nc(OC)n2CCNC(C)=O] | IA2-143 | >120 | 108 | >120 |

2.6—Inhibition of CYP

The CYP inhibition test used fluorogenic substrates specific to each CYP to check for inhibition thereof by detection of the expected metabolite using a fluorimetric method. Recombinant CYPs (CYP2B6, CYP2C8, CYP2C9, CYP2C9, CYP2C19, CYP2D6, CYP3A4) from specific humans for each cytochrome family, subfamily and polypeptide were used. The following were used as substrates: CEC (3-Cyano-7-Ethoxycoumarin) which forms as metabolite CHC (3-Cyano-7-Hydroxycoumarin); EFC (7-Ethoxy-4-trifluoromethyl coumarin), forming the metabolite HFC (7-Hydroxytri fluoromethylcoumarin); DBF (Dibenzylfluorescein) and its respective fluorescein metabolite; MFC (7-Methoxy-4-trifluoromethylcoumarin) which forms the metabolite HFC (7-Hydroxytrifluoromethylcoumarin); BFC (7-Benzyloxy-Trifluoromethylcoumarin) and its metabolite HFC; and BzRes (benzyloxyresorufin) to form resofurine. The detection of the metabolite was done with a fluorimetric method: analytical technique to identify and characterize the amount of substance by excitation using a beam of ultraviolet light and measurement of the emitted fluorescence. For detection, a 96-well plate was used. Each sample was tested in two wells (n=2) as standard condition. At least 04 wells were separated for vehicle (control). Compounds were tested at a concentration of 10M, standard for this assay. They were preincubated with a NADPH generator system in a phosphate buffer (pH 7.4) for 5 minutes at 37° C. The reaction was started by adding the specific CYP enzymes, substrate and bovine serum albumin (BSA<0.4 mg/ml). Incubations were performed between 20-50 minutes at 37° C. according to the specific parameter of each fluorogenic substrate, for the evaluated component. Fluorescence at each well was detected before and after the incubation period.

The results demonstrated that the inventive compounds do not present high affinity to the 07 cytochrome isoforms analyzed (CYP2A6, CYP2B6, CYP2C8, CYP2C9, CYP2C19, CYP2D6, CYP3A4), specially to CYP1A2, CYP isoform which agomelatine has high affinity, according to Table 5.

TABLE 5

| Chemical Structure | Code | CYP1A2 Inhibition | CYP2B6 Inhibition | CYP2C8 Inhibition | CYP2C9 Inhibition | CYP2C19 Inhibition | CYP2D6 Inhibition | CYP3A4 Inhibition * | CYP3A4 Inhibition ** |
|---|---|---|---|---|---|---|---|---|---|
| 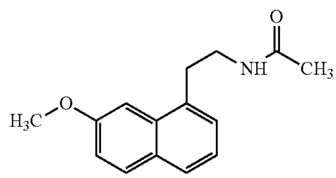 [SMILES: COc1ccc2cccc(CCNC(C)=O)c2c1] | IA2-76 | 79.8 | 1.8 | 12.9 | -19.3 | 44.4 | 7.9 | 21.6 | -0.8 |
| 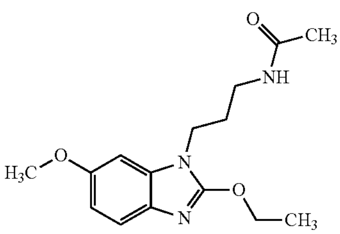 [SMILES: CCOc1nc2ccc(OC)cc2n1CCCNC(C)=O] | IA92-120 | -8.2 | 7.9 | 9.1 | 26.7 | 6.4 | -0.3 | 15.7 | 8.3 |
| 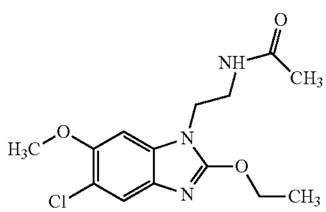 [SMILES: CCOc1nc2cc(Cl)c(OC)cc2n1CCNC(C)=O] | IA2-121 | 10.5 | 8.4 | 7 | 23.7 | 33.8 | 0.9 | 15.3 | -5.4 |
| 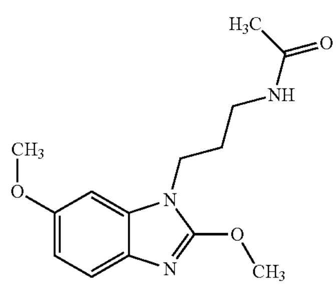 [SMILES: COc1ccc2nc(OC)n(CCCNC(C)=O)c2c1] | IA2-140 | -0.7 | 0.4 | -2.2 | 2.6 | 7.2 | 0.3 | 5.6 | 21.2 |
| 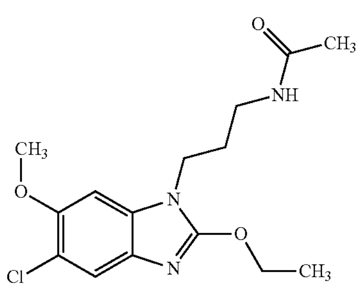 [SMILES: CCOc1nc2cc(Cl)c(OC)cc2n1CCCNC(C)=O] | IA2-142 | 12.1 | 0.5 | -4.7 | 13.0 | 27.7 | 6.9 | -1.6 | -17.6 |

TABLE 5-continued

| Chemical Structure | Code | CYP1A2 Inhibition | CYP2B6 Inhibition | CYP2C8 Inhibition | CYP2C9 Inhibition | CYP2C19 Inhibition | CYP2D6 Inhibition | CYP3A4 Inhibition * | CYP3A4 Inhibition ** |
|---|---|---|---|---|---|---|---|---|---|
| [structure: 5-chloro-6-methoxy-2-methoxy-1H-benzimidazole with N-ethyl acetamide] | IA2-143 | 1.4 | −1.1 | −13.0 | −9.6 | 10.0 | 0.8 | 2.1 | 15.9 |

2.7—Pharmacokinetics (PK) in Mouse—I.V. And Oral

PK tests were performed with CD-1 mice, using 4 animals per molecule tested, 2 animals for pharmacokinetic analysis by intravenous (IV) administration and 2 animals for oral administration. The treatment was carried out in a single dose: I.V. group with dose of 1 mg/kg and Oral group with dose of 10 mg/kg. The vehicle consisted of 5% DMSO, 30% PEG400 and 65% water. Blood collection was performed after euthanasia at 08 defined time points and at 24 hours post-dose. The pharmacokinetic analysis parameters detected for Group IV were: half-life (t½), drug concentration at time zero (C0), last measurable plasma concentration (AUClast), area under the plasma concentration curve extrapolation percentage (AUC % ext), area under the plasma concentration curve extrapolation to infinity (AUCinf), volume of distribution (Vz), steady state volume of distribution (Vss), clearance (CL) and mean residence time (MRT). The parameters evaluated for the Oral group were: bioavailability (F %), maximum concentration reached (Cmax), time to reach maximum plasma concentration (Tmax), last measurable plasma concentration (AUClast), area under the plasma concentration curve extrapolation percentage (AUC % ext), area under the plasma concentration curve extrapolation to infinity (AUCinf), area under the plasma concentration curve extrapolation to infinity versus dose (AUCinf/Dose), half-Life (t½), and mean residence time (MRT).

After intravenous administration of the compounds to mice, the inventive molecules 120, 121, 140, 142, 143 and agomelatine presented higher C0 and lower Clearance than agomelatine, highlighting the improved pharmacokinetics of the inventive molecules.

According to the results after oral administration in mice, the compounds and agomelatine showed a Tmax of 0.25 h, except compound 140 (0.375 h). In addition, all the inventive compounds showed a Cmax higher than agomelatine, being 3405, 6490, 5010, 7550, 8915 ng/ml for compounds 120, 121, 140, 142 and 143, respectively, in comparison to 21.9 ng/ml for agomelatine. In addition, the last measurable plasma concentration (AUClast) of the compounds was also higher in comparison to agomelatine. Finally, the bioavailability of the inventive compounds was considerably higher in comparison to agomelatine, being 44, 138, 71.3, 51.8 and 153% (120, 121, 140, 142 and 143) compared to 2.42% for agomelatine (Table 6).

TABLE 6

| | | | | IA2-76 (agomelatine) | IA2-120 | IA2-121 | IA2-140 | IA2-142 | IA2-143 |
|---|---|---|---|---|---|---|---|---|---|
| (A) | | | | | | | | | |
| INTRAVENOUS | Mouse | $T_{1/2}$(h) | | 0.149 | 0.237 | 0.178 | 0.296 | 0.275 | 0.187 |
| | | C0 (ng/ml) | | 811 | 1967 | 2052 | 1956 | 4129 | 2659 |
| | | CL (ml/min/kg) | | 116 | 31.2 | 29.4 | 18.8 | 10.3 | 25.5 |
| | Rat | $T_{1/2}$(h) | | 0.295 | 0.254 | 0.14 | 0.523 | 0.409 | 0.289 |
| | | CL (ml/min/kg) | | 39.1 | 48.1 | 53.3 | 26 | 16.6 | 29.8 |
| (B) | | | | | | | | | |
| ORAL | Mouse | Tmax(h) | | 0.25 | 0.25 | 0.25 | 0.375 | 0.25 | 0.25 |
| | | Cmax (ng/ml) | | 21.9 | 3405 | 6490 | 5010 | 7550 | 8915 |
| | | AUClast (h*ng/ml) | | 30.3 | 2342 | 7865 | 6137 | 8285 | 9986 |
| | | F (%) | | 2.42 | 44 | 138 | 71.3 | 51.8 | 153 |
| | Rat | AUClast (h*ng/ml) | | 1025 | 554 | 3508 | 2435 | 10892 | 4049 |
| | | F (%) | | 22.6 | 15.9 | 112 | 36.5 | 108 | 72.3 t. |

2.8—Pharmacokinetics (PK) in Rat—I.V. And Oral

PK tests were performed on Wistar-Han mice, using 4 animals per molecule tested, 2 animals for analysis of I.V. pharmacokinetics and 2 animals for analysis of oral PK. The study lasted for 2 weeks (including acclimation time and study), in which the route of administration was made by injection into the caudal vein and oral gavage. The treatment was carried out in a single dose: I.V. group with dose of 1 mg/kg and Oral group with dose of 10 mg/kg. The vehicle consisted of 5% DMSO, 30% PEG400 and 65% water. Clinical observations were made twice a day (morning and afternoon) in the pre-dose at the 08 time points defined in the protocol. Blood collection was performed after euthanasia in the pre-dose animals at 08 defined time points and at 24 hours post-dose. The pharmacokinetic analysis parameters detected for Group IV were: half-life (t½), drug concentration at time zero (C0), last measurable plasma concentration (AUClast), area under the plasma concentration curve extrapolation percentage (AUC % ext), area under the plasma concentration curve extrapolation to infinity (AUCinf), volume of distribution (Vz), steady state volume of distribution (Vss), clearance (CL) and mean residence time (MRT). The parameters evaluated for the Oral group were: bioavailability (F %), maximum concentration reached (Cmax), time to reach maximum plasma concentration (Tmax), last measurable plasma concentration (AUClast), area under the plasma concentration curve extrapolation percentage (AUC % ext), area under the plasma concentration curve extrapolation to infinity (AUCinf), area under the plasma concentration curve extrapolation to infinity versus dose (AUCinf/Dose), half-Life (t½), and mean residence time (MRT).

Following intravenous administration in rats, it was observed that the half-lives of compounds 120, 121, 140, 142, 143 and agomelatine were 0.254, 0.14, 0.523, 0.409, 0.289 and 0.295 h. And the clearance of the same compounds was 48.1, 53.3, 26, 16.6, 29.8 and 39.1 ml/min/kg, respectively. Furthermore, after oral administration to rats, compounds 120, 121, 140, 142, 143 and agomelatine showed a last measurable plasma concentration (AUClast) of 554, 3508, 2435, 10892, 4049 and 1025 h*ng/ml, respectively, and bioavailability of 15, 9, 112, 36.5, 108, 72.3 and 22.6%, respectively (Table 6). Thus, some of the inventive compounds also demonstrated higher pharmacokinetic parameters than agomelatine in Wistar-Han rats.

The invention claimed is:

1. A compound having the formula (I):

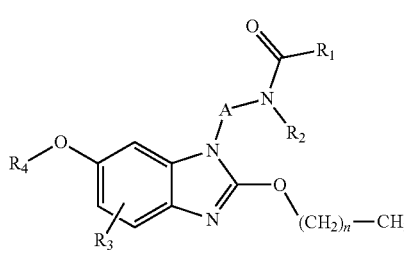

wherein

X is an oxygen or sulfur atom;

A represents a linear alkyl group of $C_{2-4}$ which may have one or more of its hydrogens replaced by an alkyl group selected from methyl, ethyl, propyl or isopropyl;

$R_1$ represents an alkyl $C_{1-6}$ or alkenyl $C_{2-6}$, alkynyl or $C_{2-6}$ or haloalkyl $C_{1-6}$, cycloalkyl or $C_{3-6}$, or $C_{1-2}$-alkyl cycloalkyl-$C_{3-6}$ group;

$R_2$ represents a hydrogen or an alkyl $C_{1-3}$ group;

$R_3$ represents a hydrogen or halogen atom;

$R_4$ represents an alkyl $C_{1-6}$ group; and n is 0 or 1.

2. The compound according to claim 1 wherein the compound is selected from the group consisting of:
N-(2-(2-ethoxy-6-methoxy-1H-benzimidazole-1-yl) ethyl)acetamide;
N-(2-(2-ethoxy-6-methoxy-1H-benzimidazole-1-yl) ethyl)propionamide;
N-(2-(2-ethoxy-6-methoxy-1H-benzimidazole-1-yl) ethyl)butyramide;
N-(2-(2-ethoxy-6-methoxy-1H-benzimidazole-1-yl) ethyl)cyclopropane carboxamide;
N-(2-(2-ethoxy-6-methoxy-1H-benzimidazole-1-yl) ethyl)cyclobutanecarboxamide;
N-(2-(2-ethoxy-6-methoxy-1H-benzimidazole-1-yl) ethyl)cyclopentane carboxamide;
N-(2-(2-ethoxy-6-methoxy-1H-benzimidazole-1-yl) ethyl)cyclohexane carboxamide;
N-(3-(2-ethoxy-6-methoxy-1H-benzimidazole-1-yl)propyl)acetamide;
N-(3-(2,6-dimethoxy-1H-benzimidazole-1-yl)propyl)acetamide;
N-(2-(2,6-dimethoxy-1H-benzimidazole-1-yl)ethyl) acetamide;
N-(2-(2,6-dimethoxy-1H-benzimidazole-1-yl)ethyl)propionamide;
N-(2-(2,6-dimethoxy-1H-benzimidazole-1-yl)ethyl)butyramide;
N-(1-(2-Ethoxy-6-methoxy-1H-benzimidazole-1-yl)propan-2-yl)acetamide;
2-Bromo-N-(2-(2-ethoxy-6-methoxy-1H-benzimidazole-1-yl)ethyl)acetamide;
N-(2-(6-methoxy-2-(methylthio)-1H-benzimidazole-1-yl)ethyl)acetamide;
N-(2-(5-bromo-2-ethoxy-6-methoxy-1H-benzimidazole-1-yl)ethyl)acetamide;
N-(2-(5-chloro-2-ethoxy-6-methoxy-1H-benzimidazole-1-yl)ethyl)acetamide;
N-(3-(5-chloro-2-ethoxy-6-methoxy-1H-benzimidazole-1-yl)propyl)acetamide;
N-(3-(5-chloro-2,6-dimethoxy-1H-benzimidazole-1-yl) propyl)acetamide;
N-(2-(5-chloro-2,6-dimethoxy-1H-benzimidazole-1-yl) ethyl)acetamide;
N-(2-(5-chloro-2-ethoxy-6-methoxy-1H-benzimidazole-1-yl)ethyl)cyclopropanecarboxamide; and
N-(2-(7-chloro-2-ethoxy-6-methoxy-1H-benzimidazole-1-yl)ethyl)acetamide.

3. A process for obtaining a compound according to claim 1 comprising:
(a) reacting the compound of formula (III)

with a carboxylic acid anhydride of formula (IV)

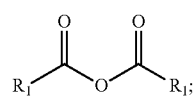

or with a carboxylic acid halide of formula (V)

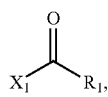
(V)

wherein $R_1$, $R_2$ and $R_4$ are as described in claim 1 and $X_1$ is a halogen selected from the group consisting of chlorine and bromine, to provide a compound of formula (VI)

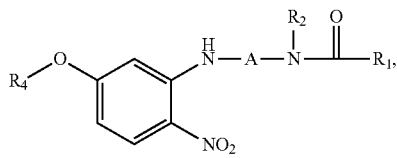
(VI)

(b) reacting the compound (VI) obtained in (a) with a reducing agent to obtain the compound of formula (VII)

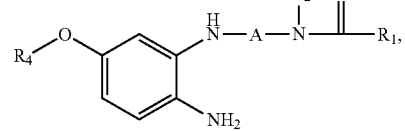
(VII)

(c) reacting of the compound (VII) obtained in (b) with a tetraalkylorthocarbonate selected from the group consisting of tetramethylorthocarbonate and tetraethyl orthocarbonate, to obtain the compound of formula (Ia):

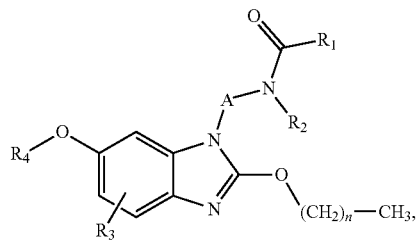
(Ia)

wherein $R_3$ corresponds to a hydrogen atom and "n" corresponds to zero or one; and (d) reacting the compound of formula (Ia) obtained in (c) with a halogenating agent selected from the group consisting of N-bromosuccinimide, N-chlorosuccinimide and N-iodosuccinimide, to obtain the compound of formula (Ia) wherein $R_3$ is a halogen selected from the group consisting of bromine, chlorine and iodine.

4. A process for obtaining a compound according to claim 1 comprising:

(a) reacting a compound of formula (III)

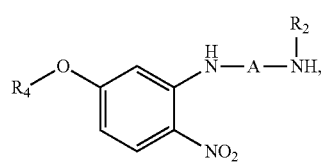
(III)

with a carboxylic acid anhydride of formula (IV)

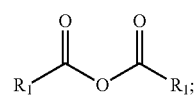
(IV)

or with a carboxylic acid halide of formula (V)

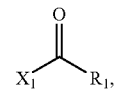
(V)

wherein $R_1$, $R_2$ and $R_4$ are as described in claim 1 and $X_1$ represents a halogen selected from the group consisting of chlorine and bromine, to obtain a compound of formula (VI)

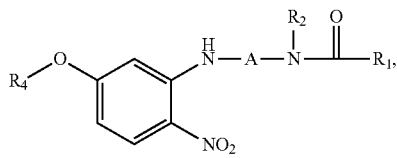
(VI)

(b) reacting the compound (VI) obtained in (a) with a reducing agent to obtain the compound of formula (VII)

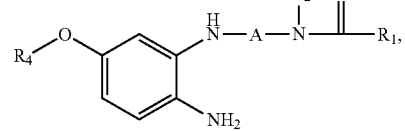
(VII)

(e) reacting of compound (VII) obtained in (b) with thiourea to obtain the compound (VIII)

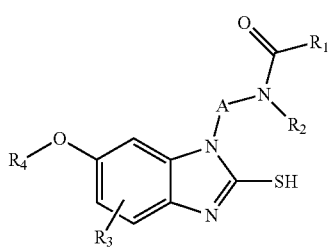

wherein $R_3$ represents a hydrogen atom;
(f) reacting the compound (VIII) obtained in (e) with an alkylating agent to obtain the compound of formula (Ib)

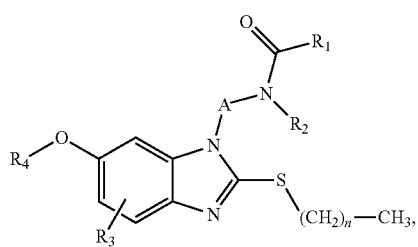

wherein $R_3$ represents a hydrogen atom and "n" represents zero or one; and
(g) reacting the compound of formula (Ib) obtained in (f) with a halogenating agent selected from the group consisting of N-bromosuccinimide, N-chlorosuccinimide and N-iodosuccinimide, to obtain the compound of formula (Ib) wherein $R_3$ represents a halogen selected from the group consisting of bromine, chlorine and iodine.

5. A pharmaceutical composition comprising:
a) at least one compound of formula (I)

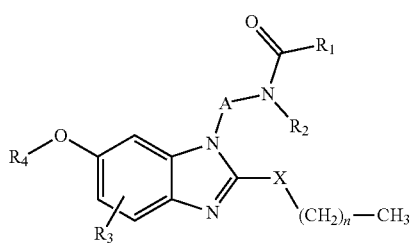

wherein
X corresponds to an oxygen or sulfur atom;
A corresponds to a linear alkyl $C_{2-4}$ group, which may have one or more of its hydrogens substituted by an alkyl group selected from methyl, ethyl, propyl or isopropyl;

$R_1$ is an alkyl $C_{1-6}$, or alkenyl $C_{2-6}$, or alkynyl $C_{2-6}$, or haloalkyl $C_{1-6}$, or cycloalkyl $C_{3-6}$, or $C_{1-2}$-alkyl-$C_{3-6}$ cycloalkyl group;
$R_2$ is a hydrogen or a alkyl $C_{1-3}$ group;
$R_3$ corresponds to a hydrogen or a halogen atom;
$R_4$ is a alkyl $C_{1-6}$ group; and
n is 0 or 1; and
b) a pharmaceutically acceptable vehicle.

6. The pharmaceutical composition according to claim 5 wherein the compound of formula (I) is selected from the group consisting of:
N-(2-(2-ethoxy-6-methoxy-1H-benzimidazole-1-yl) ethyl)acetamide;
N-(2-(2-ethoxy-6-methoxy-1H-benzimidazole-1-yl) ethyl)propionamide;
N-(2-(2-ethoxy-6-methoxy-1H-benzimidazole-1-yl) ethyl)butyramide;
N-(2-(2-ethoxy-6-methoxy-1H-benzimidazole-1-yl) ethyl)cyclopropane carboxamide;
N-(2-(2-ethoxy-6-methoxy-1H-benzimidazole-1-yl) ethyl)cyclobutanecarboxamide;
N-(2-(2-ethoxy-6-methoxy-1H-benzimidazole-1-yl) ethyl)cyclopentane carboxamide;
N-(2-(2-ethoxy-6-methoxy-1H-benzimidazole-1-yl) ethyl)cyclohexane carboxamide;
N-(3-(2-ethoxy-6-methoxy-1H-benzimidazole-1-yl)propyl)acetamide;
N-(3-(2,6-dimethoxy-1H-benzimidazole-1-yl)propyl)acetamide;
N-(2-(2,6-dimethoxy-1H-benzimidazole-1-yl)ethyl)acetamide;
N-(2-(2,6-dimethoxy-1H-benzimidazole-1-yl)ethyl)propionamide;
N-(2-(2,6-dimethoxy-1H-benzimidazole-1-yl)ethyl)butyramide;
N-(1-(2-Ethoxy-6-methoxy-1H-benzimidazole-1-yl)propan-2-yl)acetamide;
2-Bromo-N-(2-(2-ethoxy-6-methoxy-1H-benzimidazole-1-yl)ethyl)acetamide;
N-(2-(6-methoxy-2-(methylthio)-1H-benzimidazole-1-yl)ethyl)acetamide;
N-(2-(5-bromo-2-ethoxy-6-methoxy-1H-benzimidazole-1-yl)ethyl)acetamide;
N-(2-(5-chloro-2-ethoxy-6-methoxy-1H-benzimidazole-1-yl)ethyl)acetamide;
N-(3-(5-chloro-2-ethoxy-6-methoxy-1H-benzimidazole-1-yl)propyl)acetamide;
N-(3-(5-chloro-2,6-dimethoxy-1H-benzimidazole-1-yl)propyl)acetamide;
N-(2-(5-chloro-2,6-dimethoxy-1H-benzimidazole-1-yl)ethyl)acetamide;
N-(2-(5-chloro-2-ethoxy-6-methoxy-1H-benzimidazole-1-yl)ethyl)cyclopropane carboxamide; and
N-(2-(7-chloro-2-ethoxy-6-methoxy-1H-benzimidazole-1-yl)ethyl)acetamide.

* * * * *